United States Patent
Ozeki et al.

(10) Patent No.: US 7,811,488 B2
(45) Date of Patent: Oct. 12, 2010

(54) METHOD FOR MANUFACTURING MOLDED ARTICLE WITH CORE

(75) Inventors: Yuichi Ozeki, Nagoya (JP); Yoshiya Kondo, Nagoya (JP); Yukinao Watanabe, Nagoya (JP)

(73) Assignee: Sanwa Kagaku Kenkyusho Co., Ltd, Nagoya (JP)

( * ) Notice: Subject to any disclaimer, the term of this patent is extended or adjusted under 35 U.S.C. 154(b) by 319 days.

(21) Appl. No.: 10/317,360

(22) Filed: Dec. 12, 2002

(65) Prior Publication Data

US 2004/0113319 A1 Jun. 17, 2004

Related U.S. Application Data

(63) Continuation of application No. PCT/JP01/05296, filed on Jun. 20, 2001.

(30) Foreign Application Priority Data

| Jun. 20, 2000 | (JP) | 2000-183996 |
| Dec. 20, 2000 | (JP) | 2000-387052 |
| Feb. 20, 2001 | (JP) | 2001-042787 |
| Mar. 15, 2001 | (JP) | 2001-074413 |
| Mar. 30, 2001 | (JP) | 2001-098571 |
| Apr. 24, 2001 | (JP) | 2001-125690 |

(51) Int. Cl.
*A61J 3/00* (2006.01)
*A61J 3/06* (2006.01)
*A61J 3/10* (2006.01)
*A61K 9/20* (2006.01)
*A61K 9/28* (2006.01)
*B30B 11/02* (2006.01)
*B30B 11/08* (2006.01)
*B30B 15/30* (2006.01)
*B30B 11/00* (2006.01)

(52) U.S. Cl. .................. 264/113; 264/112
(58) Field of Classification Search .......... 264/109–128
See application file for complete search history.

(56) References Cited

U.S. PATENT DOCUMENTS 1,624,904 A * 4/1927 Claus .................. 264/319

(Continued)

FOREIGN PATENT DOCUMENTS

GB 743222 1/1956

(Continued)

OTHER PUBLICATIONS

PCT International Search Report for Kondo, et al., Int'l Application No. PCT/JP01/05296, Filed Jun. 20, 2001, Dated Sep. 17, 2001.

*Primary Examiner*—Christina Johnson
*Assistant Examiner*—Patrick Butler
(74) *Attorney, Agent, or Firm*—Hiroe & Associates; Taras P. Bemko

(57) ABSTRACT

A method for manufacturing a molded article with at one or more cores uses compression molding apparatus that includes upper and lower punches that have a double structure comprising a central punch and an outer punch that surrounds the periphery of the central punch. The central punch and the outer punch are capable of independent sliding motions and compressing operations. Molding materials are supplied for a core and an outer layer respectively. The molding materials are compressed by the punches to form molded articles that include the core. The method may be executed in a rotary compression molding machine.

3 Claims, 14 Drawing Sheets

Figure 1:
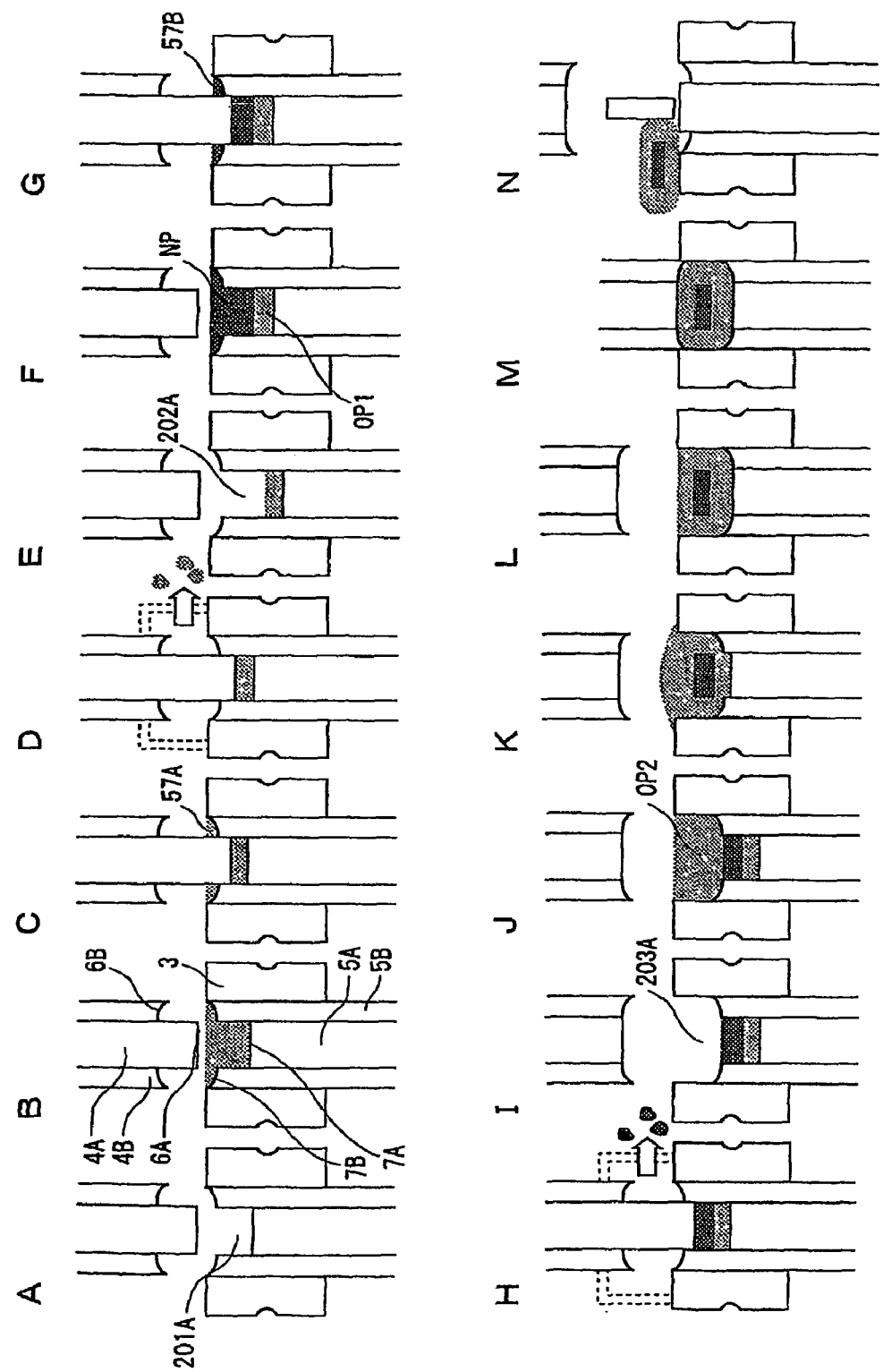

U.S. PATENT DOCUMENTS 5,071,607 A   12/1991   Ayer et al.

FOREIGN PATENT DOCUMENTS

| GB | 839502 | * | 6/1960 |
| GB | 1034713 | | 4/1963 |
| GB | 1034713 | * | 6/1966 |
| JP | 59-39499 | | 3/1984 |
| JP | 02-243157 | * | 9/1990 |
| JP | 1-30537 | | 10/1990 |
| JP | 07-214396 | | 8/1995 |
| JP | 2000-61699 | | 2/2000 |

* cited by examiner (A)

(B)

(A)

(B)

(C)

METHOD FOR MANUFACTURING MOLDED ARTICLE WITH CORE

This application is a continuation application of PCT Application No. PCT/JP01/05296, filed Jun. 20, 2001, which claims priority of Japan Application Nos. 2000-183996, filed Jun. 20, 2000, 2000-387052, filed Dec. 20, 2000, 2001-42787, filed Feb. 20, 2001, 2001-74413, filed Mar. 15, 2001, 2001-98571, filed Mar. 30, 2001, and 2001-125690, filed Apr. 24, 2001, the contents of which are incorporated by reference here into this application.

Throughout this invention, various references are cited. Disclosures of these publications in their entireties are hereby incorporated by reference into this application to describe more fully the state of the art to which this invention pertains.

FIELD OF THE INVENTION

The present invention relates generally to a manufacturing method for manufacturing a molding by compressing molding material such as powder granule, an apparatus for use in the method, and a molding which is the product thereof, and more particularly, to a method for manufacturing a molding with core, a rotary compression molding machine for use in practicing the method, and a molding with core which is the product thereof.

BACKGROUND OF THE INVENTION

The method to manufacture a molding by compacting molding material represented by powder granule, etc., has widely been used in various industrial fields for example not only in the field of medicines and foods (functional foods and general foods), but also in the field of electronic material such as semiconductor sealing resin molding, molding of battery related products, molding of powder metallurgy related products, and molding of electronic functional parts as well as in the field of agricultural chemicals and sanitary products.

In the field of medicines, especially in case of medicines for oral administration, a solid molding called "tablet" is one of the most widely used form of medicines, because of their various merits, e.g., they are simple to manufacture and easy to take. Among them, a molding having core therein is called compression-coated tablet because it is each manufactured by distributing and compacting the powder granule as an outer layer around the core (center tablet).

Since the compression-coated tablet having a core therein can separate medicines that undergo change of formulation into the core and the outer layer, an improved stability is expected due to low probability of contact between medicines. Besides the compression-coated tablet present an effective way to mask bitter taste of core and improve appearance of tablet, as well as to protect against damaging environmental factors (such as light or humidity). They can also be used as release controlled medicines that include an outer layer having a rapid releasability and a core in the form of an enteric tablet or a sustained release tablet.

Up until now, when manufacturing a molding with core such as a compression-coated tablet, the core was made as a molded piece in advance in a separate tableting machine, then it was moved to a die of a different compression-coated tablet machine where the powder granule forming the outer layer was fed and then compressed. For this reason, compared to the typical method for manufacturing compression moldings, this method presents some serious problems such as more steps and low productivity.

Besides, in this conventional method feeding cores as molded pieces, since the molded pieces as cores are to be fed one by one in the die of a rotary table which revolves at a high speed, sometimes a core may not be fed and sometimes they may be fed in excess and therefore problems such as manufacturing of products without core or products with plural cores occur easily. For this reason, in order to preserve quality, there appear a necessity for complicated mechanisms and systems for surveillance of the feeding of core and inspection of the final molding. Thus the machines engaged in the process of manufacturing of a molding with core become larger in size and more complicated.

Besides, in the traditional method of feeding the core, it was important that the core was horizontally disposed in the middle of the outer layer powder granule within the die and then compression-molded. For this reason some moldings disorders occur very easily. For example when the core is not in the middle, the outer layer becomes thinner in that region; also the capping occurs because of decline in the moldability. Another disorder is a lamination when cracks on the surface of the molding appear in layers.

In order to prevent offset in the centering of the core due to the centrifugal force of the rotary table, Japanese Patent Laid-open Pub. No. Sho55-48653 discloses an inspection method of the centering of the core by visual inspection after it is fed; Japanese Patent Laid-open Pub. No. Sho61-60298 discloses a system provided with a multi-optical-axis identification sensor in conjunction with core feeder to automatically correct the core position; and Japanese patent Laid-open Pub. No. Hei9-206358 discloses a method for preventing the offset in the core centering by use of a system for automatically correcting the core feeding positions on the basis of information acquired from a CCD imaging device.

However, even when the above core centering systems are used, problems of precision of the centering and stability of feeding of cores still remain unsolved and therefore step of the high-speed rotary table as in the ordinary tableting machines (40 to 60 rpm) is difficult, so the actual operating ability is limited to approx. 30 rpm and the productivity is low.

In regard to the size of a molding with core, in the conventional method, due to dispersions in the core centering and to insufficient adhesion strength between the core and the outer layer which may arise from utterly separate molding of the core and the outer layer, the outer layer minimum thickness of 1 to 1.5 mm is required, and inevitably, a molding with core becomes at least 2 to 3 mm larger than the core itself. Therefore compared to coreless a molding, the molding with core has the tendency to become larger, which is an obstacle in the efforts to miniaturize the molding.

As far as the shape of core is concerned, in the traditional method in which cores are externally fed, it is necessary to provide a dedicated feeder, conforming to the shape of the core. Therefore, when manufacturing a molding with diversely shaped cores, a diversity of core feeder is needed and the problem of lacking in versatility still remains left.

In the traditional method, since a core prepared beforehand is fed, it is necessary for the cores to have moldability that will allow an harmless delivery through a supply line into the die, as well as shape that will allow smooth passage. Therefore there are some limitations in the shape and properties of the core. For example, the traditional method does not provide a way to manufacture a molding having a core that is not the solid or a core that is the very powder granule.

As far as the shape of the punch in the prior art is concerned, different types of punches are used, depending on the shape of the molding to be compressed. In some instances, punches with specific shape are used. For example, in case of a troche-shaped molding, used in medical field, in which the central part is cut out, it is very difficult to fill in evenly the powder granule, using an ordinary punch. Also, to open the central part, a so-called ring-punch, or a double punches is used for the compression molding.

When manufacturing extremely small and complex in a shape molding used in diverse applications including electronic parts, due to the complexity in the shape, there is a difference in the compression ratio of the powder granule. Because of this difference, the molded products may have largely different powder granule densities, depending on the sites, with the result that the molding is easily broken or damaged. Thus, in order to solve these problems, a method has been executed in which powder granule is filled in such that the powder granule densities of the molding are the same by separately moving the bottom center punch and the lower outer punch, of multiple punches having the same structure as the ring punch which is seen in the lower punch structure of the rotary powder compression molding machine disclosed in Japanese Patent Laid-open Pub. No. Sho52-126577.

However, the conventional so-called ring punch, i.e., punch having a multiple-structure is used as an additional aid for filling the powder granule and to secure ring-shaped cavities and that is why it is utilized mainly as lower punch. Even the center punch is used in stationary mode.

The manufacturing methods and apparatus for molding having a single core are subjected to the above situations and problems. However, in regard to a molding having plural cores, since in the state of the art any rotary tableting machines that can manufacture such a molding does not exist, there are no prior art of practical use.

In terms of references, Japanese Patent Pub. No. Hei2-243158 describes a method for reducing the size of a compression-coated tablet by introducing plural small-sized core pellets into a single die. However, in addition to involving the above situations and problems of the molding with single core, there are some new problems due to increase in the manufacturing process steps. For example, there also increases the frequency of manufacturing of a molding without core or with more than one core as set forth above. In other instances, due to interference among cores in the die, the positions of different cores are not consistent, but are different for each molding.

Following is a reference to the prior art related to a molding. As described above, the method to manufacture compression-coated tablets consisted of feeding cores, prepared in advance in a different tableting machine, into a die, feeding the outer layer around the core and then applying compression. For this reason, the core was restricted by some physical factors, mainly the moldability (friability and hardness) for allowing the supply into the die. Therefore due to problems of handling and poor feeding ability of the core caused by wearing away of cores, only cores with high moldability were used in this method.

In order to change the formulation to improve moldability of the core, a conventional method has been employed, namely to reduce the amount of molding material with poor moldability, or on the contrary to increase the amount of molding material with high moldability. In other words, since the active medicine ingredients (effective ingredients or main ingredients) commonly possess poor moldability, there were only two alternatives either to reduce the amount of effective ingredients of the core, or to improve wear resistance by feeding large amount of excipients etc., to increase the weight of the core.

In case of the traditional compression-coated tablet, since more or less, offset in positioning of the fed core occurs, it was difficult to reduce the thickness of the outer layer, which was one of the reasons for the rather large size of a compression-coated tablet.

Similar problems with the moldability also exist in the field of the so-called conventional tablet, manufactured by compressing mixture of effective ingredients and excipients, etc. Since in most cases effective ingredients are actually ingredients with poor moldability, under the existing circumstances the methods to improve the moldability are, just like in the above described case with the compression-coated tablet, only two either to decrease the ratio of addition of the effective ingredients in the formulation, or to increase the ratio of addition of excipients, etc., for the improvement of the moldability, ignoring the fact that this will enlarge the size of the tablet.

Sill, there is another method to improve the moldability of some ingredients with poor moldability by granulation, etc. However, considering the influence of the granulation solvent over the stability and the increase in costs due to increase in the number of the manufacturing process steps and also considering the fact that even after granulation the moldability of some ingredients do not improve, this method cannot be used as means for fundamentally modifying the moldability of all ingredients. Much more essential is the improvement achieved through modifying the composition of ingredients and diminishing the concentration of effective ingredients.

Therefore, at present there are only two methods to improve the moldability of molding containing ingredients with poor moldability either to decrease the ratio of ingredients with poor moldability which occupy in the formulation, or to feed large amount of ingredients that improve the moldability and thus increase total weight of products.

However, especially in pharmaceutics, the dosage of effective ingredients is strictly fixed and therefore, in case that the effective ingredients have poor moldability, the only two options are either to decrease the amount of those effective ingredients per tablet and to increase the number of tablets to be taken, or, without increasing the number of tablets to be taken, just to enlarge the size of the tablets. This often caused problems with swallowing, especially among older people and infants.

Next follows description of prior art for manufacture of a molding that contain granular molding material, which are highly brittle and lacking moldability, such as microcapsules and various coated granule, used in pharmaceutics and food industry. However, description herein on such granular molding material will be limited to microcapsules.

In microcapsules, the granulated ingredients are protected from external influences and therefore it can be expected that their stability will increase and any possibility for undesired reaction with other ingredients in the same mixture will be eliminated. The solidification of liquid active drug or low-melting-point active drug can be made to a tablet, and they can also prevent oxidation reactions as well as photolytic reactions, and combination alterations thereof and thus increase the stability of the active drug compounds. Furthermore, they can also control the reactions of the active drug in a living body. For example, when solution, made by dissolving of insoluble active drug into solvent, is enclosed in capsules, its absorption efficiency in the living body is improved. Or, by capsulation of one of the ingredients, susceptible to chemical reactions, it is isolated and allowed to enter chemical reactions only after being used. Furthermore, liquid products are inconvenient to be utilized, therefore they are made into apparently solid particle or powder and thus by improving their weight and handling properties make them suitable for feeding into confectionery, cosmetics and agricultural chemicals. In other words, the area of application of granulated molding material is indeed very wide.

The term "microcapsules" broadly includes besides the microcapsules themselves, also seamless capsules, mini soft capsules, micro spheres (micro beads) etc. The range of their utilization in pharmaceutics depends on their size, shape and characteristics. They can be used as multiple-kinds of active drugs that are consumed at once, such as multivitamins. Since there are special microcapsules such as sustained release microcapsules and enteric-coated microcapsules, they can also be fed to active drugs as controlled release preparations.

Up to now, when intended for oral administration, in most cases those microcapsules were manufactured as capsule preparations, filled into hard capsules, due to their easy handling properties. This made them very expensive as well as difficult to take. Not only this, but gelatin capsules, that enclosed microcapsules, were easy to be tempered and often were infected with foreign bodies, which could cause unfortunate accidents. For this reason many efforts were put to develop a method that would allow avoiding the use of gelatin capsules and enable turning the microcapsules into tablets.

Thus, turning the microcapsules into tablets has some advantages especially in the fields of pharmaceutics and food industry. However the manufacturing method for tablets, containing microcapsules, which was based on the prior art, presented two major problems. The first one is the decline in hardness and wear-resistant properties of tablets, due to lack of moldability in microcapsules themselves. The second one is the increase in variation of the microcapsules' content in tablets, due to separation or segregation of microcapsules and excipients during tabletting process.

Tablets containing microcapsules is disclosed in Japanese Patent Laid-open Pub. Nos. Sho50-36619, Sho53-142520, Hei2-72113, Hei2-237914, Hei9-52847 and 2000-16932. In general, however, microcapsules are coreless structures made of encapsulated in gelatin lipid-soluble or water-soluble ingredients as active drug. For this reason, when high physical pressure is applied from outside, the coating gets broken and the active drug ingredients are released.

Next, the coating of the microcapsules is made of gelatin which is an ingredient with poor moldability, and hence, when compared with excipients, used in pharmaceutics and food industry, the microcapsules are extremely poor in moldability. Such poor moldability is attributable to the poor plastic deformability of the microcapsules themselves. On the contrary, this characteristic makes it possible to maintain the shape of capsules even inside tablets.

Furthermore, shape of other capsules, such as seamless capsules and micro-spheres, is smooth surfaced perfect sphere and, combined with the fact that the ingredient of the coating is gelatin, which has poor moldability at tabletting, it makes manufacturing of tablets as single units impossible.

Thus, when microcapsules, that completely lack moldability, are molded together with excipients, in order to improve this lack of moldability, it is necessary to apply high tabletting pressure during tabletting process. However, the tabletting with a high pressure might lead to new problems, such as breaking of the microcapsule coating. So at present the manufacturing process is stuck in a situation in which increasing pressure in order to improve moldability will cause breaking of the microcapsule coating, and on the other hand decreasing pressure in order to prevent destruction of the coating will result in insufficient moldability.

In order to secure the moldability and prevent the destruction of the coating due to increased compression stress upon tabletting, the microcapsules are sandwiched between layers, formed by granulated excipients and a layer of excipients is used as a buffer-agent against compression during the tabletting process. This technique is disclosed in Japanese Patent laid-open Pub. No. Sho50-36619. In Japanese Patent Laid-open Pub. No. Sho53-142520 there is disclosed a description that lactose, ordinary crystalline cellulose and starch in large amounts can be used as excipients. Crystalline cellulose is described herein to be especially effective as excipients. Furthermore, in Japanese Patent Laid-open Pub. No. Sho61-221115 is disclosed a method, employing about 10 to 50% ordinary crystalline cellulose.

However, when manufacturing such tablets, there are two options either to decrease the microcapsules content by amount, i.e., the amount of the active drug contained therein, or to feed large amount of excipients in order to keep a predetermined amount of active drug or microcapsules containing the predetermined amount of the active drug. In other words, it is practically impossible to manufacture tablets with high content of microcapsules. In case of medicines for example, the amount of the active drug that must be contained in one tablet or one dosage depends on the efficacy of this active drug and therefore the amount of the active drug cannot be reduced. As a result, the amount of the excipients is increased and the tablets become intolerably large in size.

There is also a different method to achieve moldability by granulating microcapsules with a binder and/or suitable excipients. Japanese Patent Laid-open Pub. No. Hei9-52847 discloses a tablet manufacturing method by wet mixing granulation. Another tablet manufacturing method using similar techniques for wet mixing granulation is disclosed in Japanese Patent Laid-open Pub. No. 2000-16932. However, tablets that contain 28% microcapsules of this embodiment had 1% friability (in accordance with Japanese Pharmacopoeia) and not very good moldability. Furthermore, the mixing granulation method, in which the granule is formed by high-speed rotation of blades and kneading, involves some problems such as destruction of the microcapsules during granulation steps. Besides, gelatin, which is the main material for microcapsules, swells at contact with water and so it would be difficult in terms of steps and qualities to use water as the granulation solvent. Therefore ethanol or other organic solvents should be used as granulation solvent, which leads to new problems such as increase of the production costs and residual solvent in the manufacturing environment and in the product itself.

Thus, it is very difficult to manufacture tablets that contain large amount of microcapsules, using the traditional methods. The problem is not only the moldability of the tablets, but also the dispersion of microcapsule content in the tablet, caused by the dissociation or segregation of the microcapsules and the excipients during the process of tablet forming.

In general, granulated bodies, containing large particles like microcapsules and small particles like excipients, differ in friction coefficient, depending on the size of the particles and the state of their surface. For this reason, due to movement and vibration of the rotary table during the process of tablet formation, the granulated bodies are often separated into large particles and small particles. Thus the granulated bodies are divided into a group of large size particles and a group of small size particles (particle size segregation). Furthermore, since the microcapsules and the excipients also differ in density, it is easy to cause segregation due to density difference (density segregation).

Due to these two segregation factors, as the time for tablet formation elapses, the product also undergoes separation or segregation. As a result, the separated or segregated tablet material is fed and molded in a die, so the amount of microcapsules in the tablets undergoes a change. There are two methods to prevent the separation or segregation described above. The first one is to granulate the microcapsules and the excipients and make them one particle. The second one is to decrease the content of microcapsules and feed the tablet material into a die before the separation or segregation occurs. However, the first granulation method presents some problems such as problems of the above-described solvent and increase in the cost, as well as insufficient moldability. The second method also cannot provide a substantial solution to all problems, as it just reduces the separation or segregation, but in doing so it makes impossible to prescribe large amounts of microcapsules.

In case of the traditional molding, containing microcapsules, the microcapsules more or less come to the surface of the molding and problems such as desorption of the microcapsules from the molding cannot be avoided. Problems such as poor moldability and friability also remain unsolved.

DETAILED DESCRIPTION OF THE FIGURES

Figure 2:
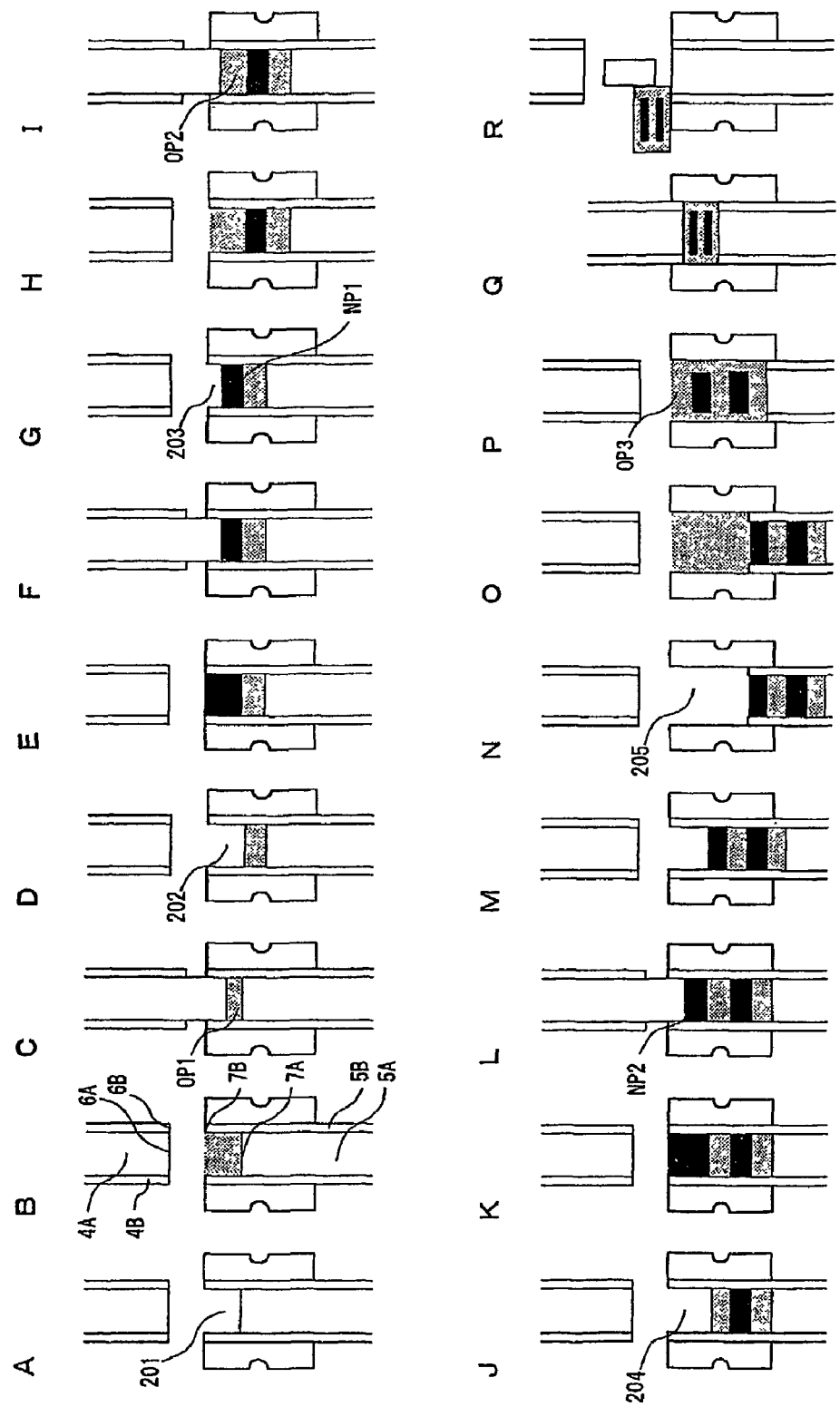
Figure 3:
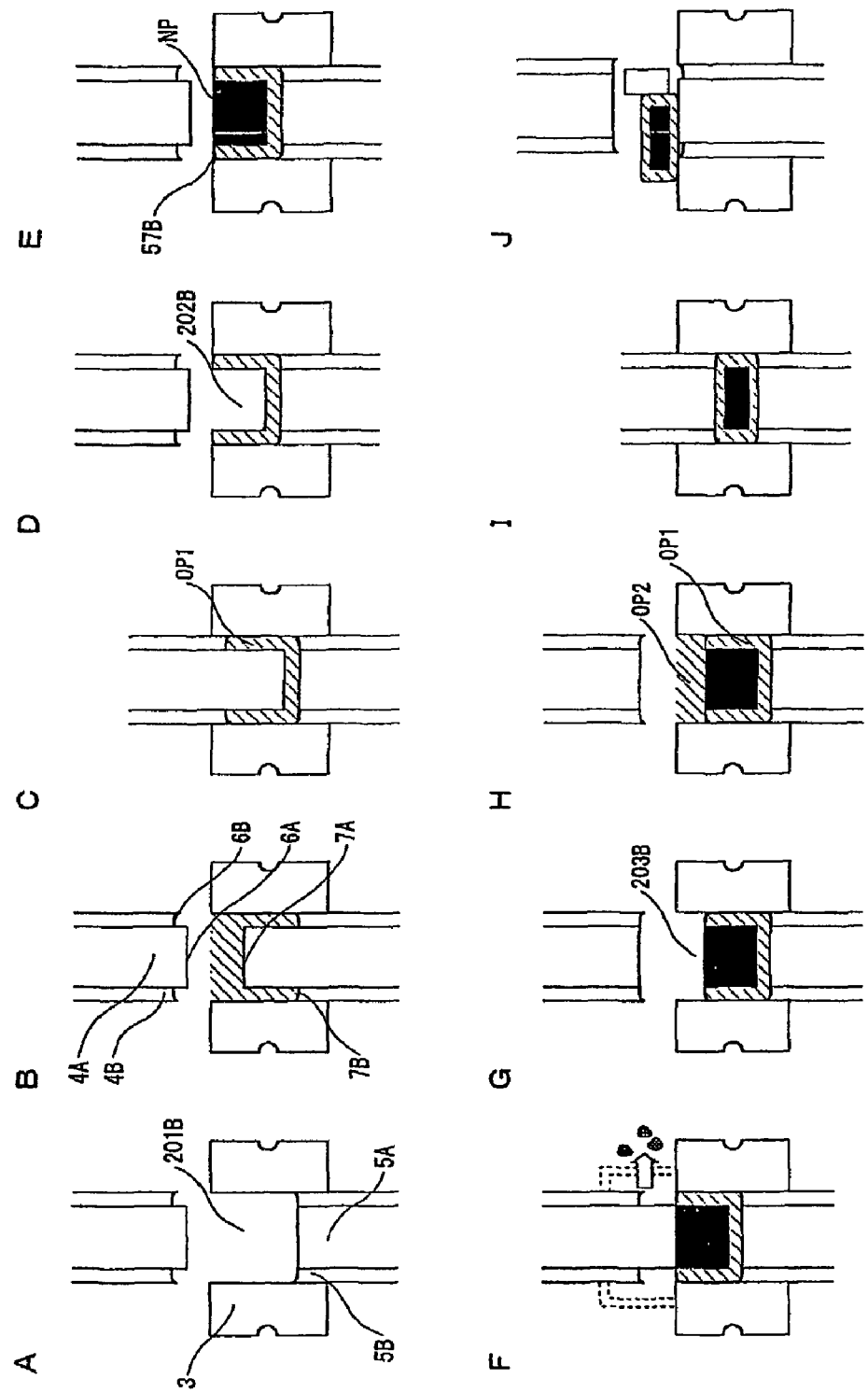
Figure 4:
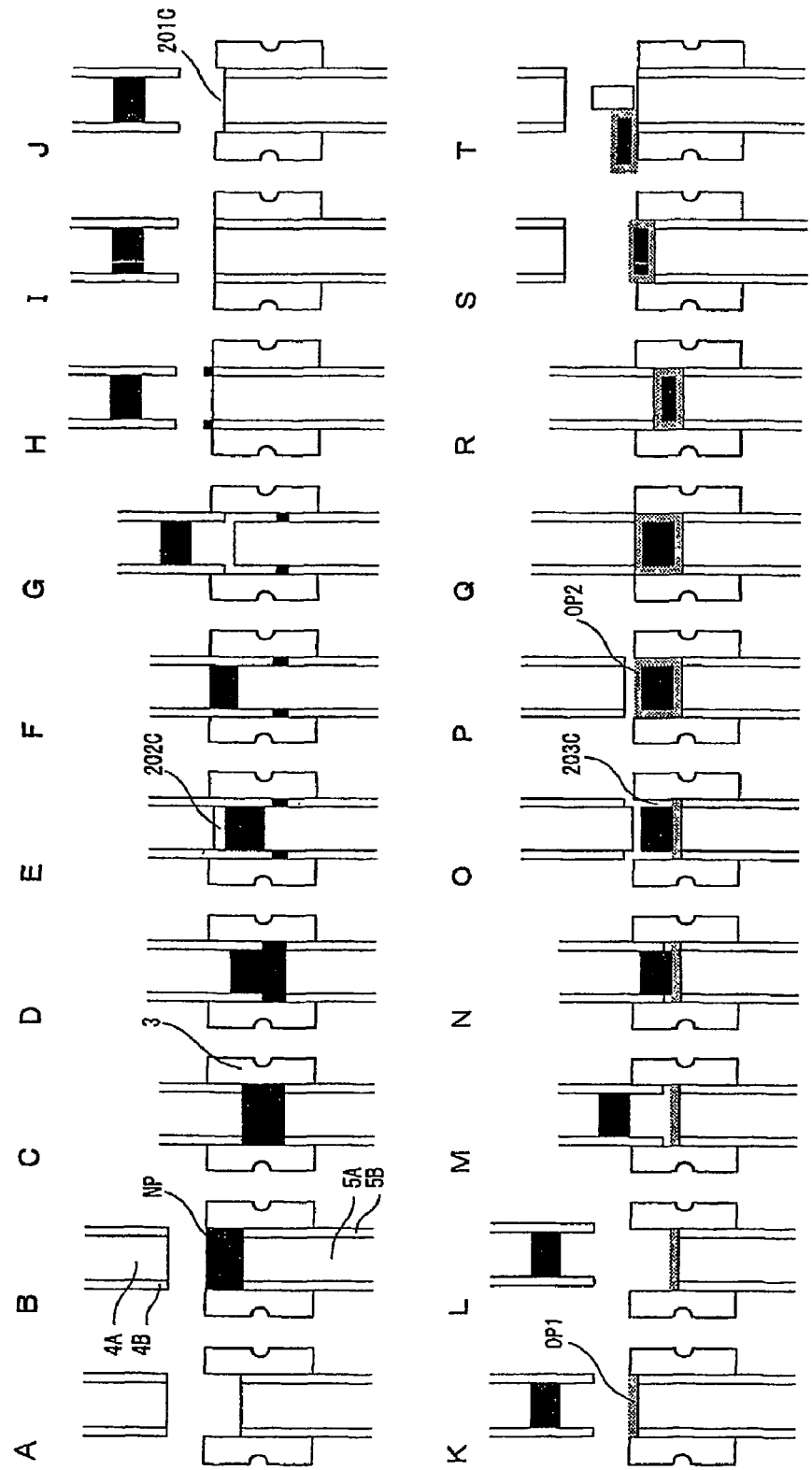
Figure 5:
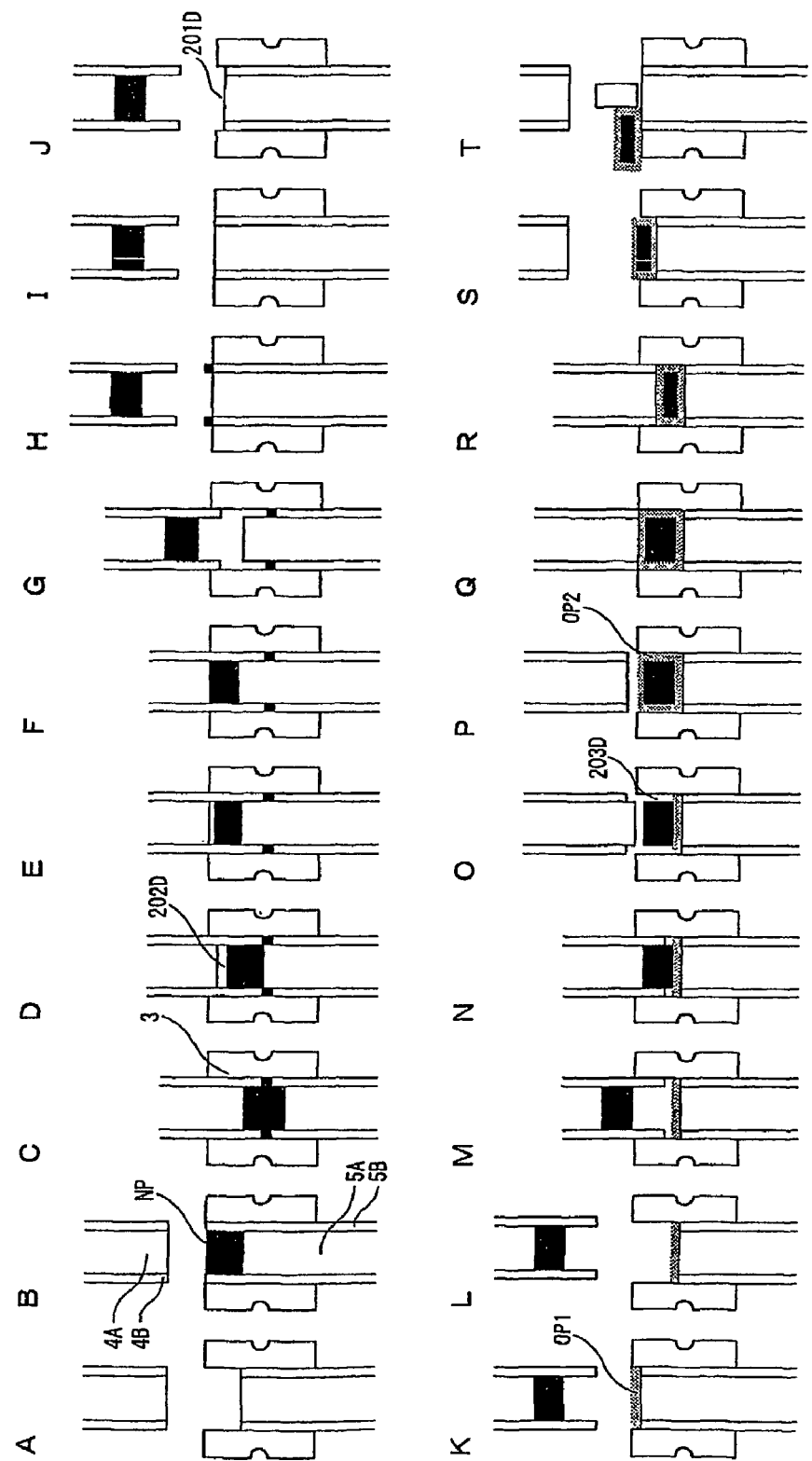
Figure 6:
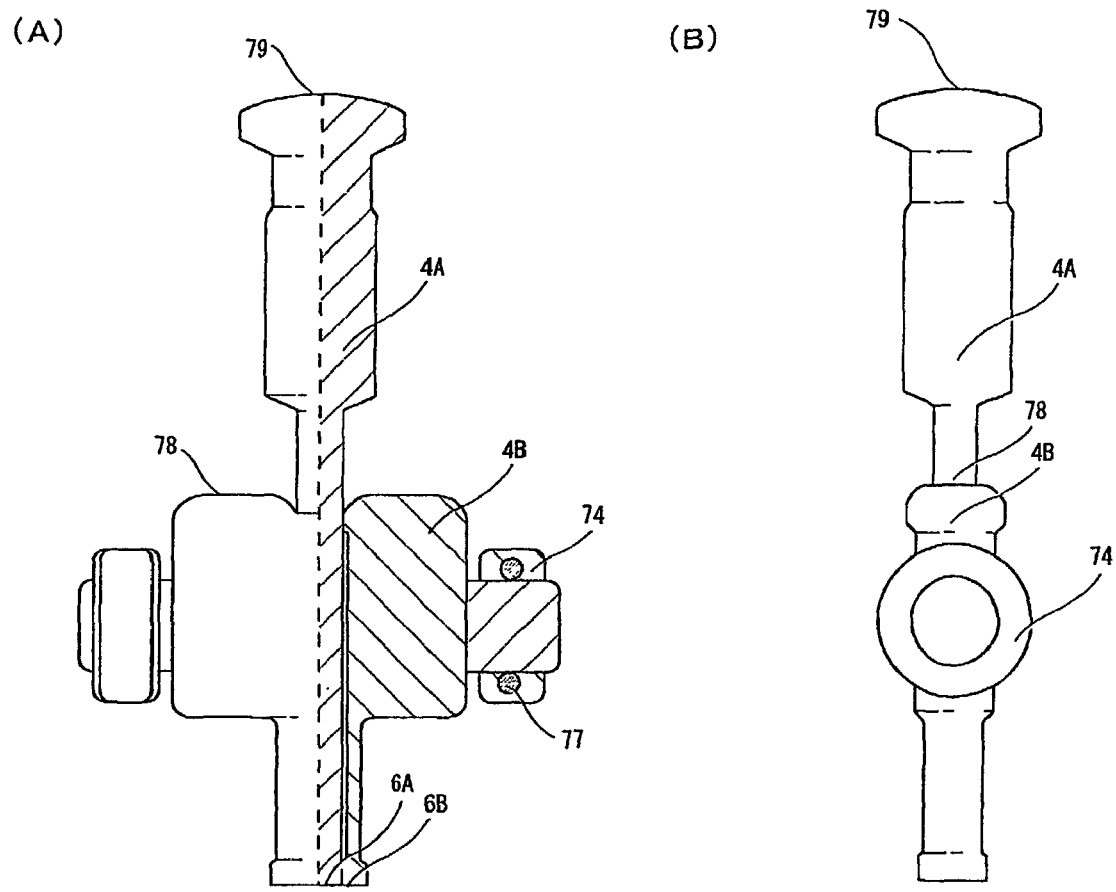
Figure 7:
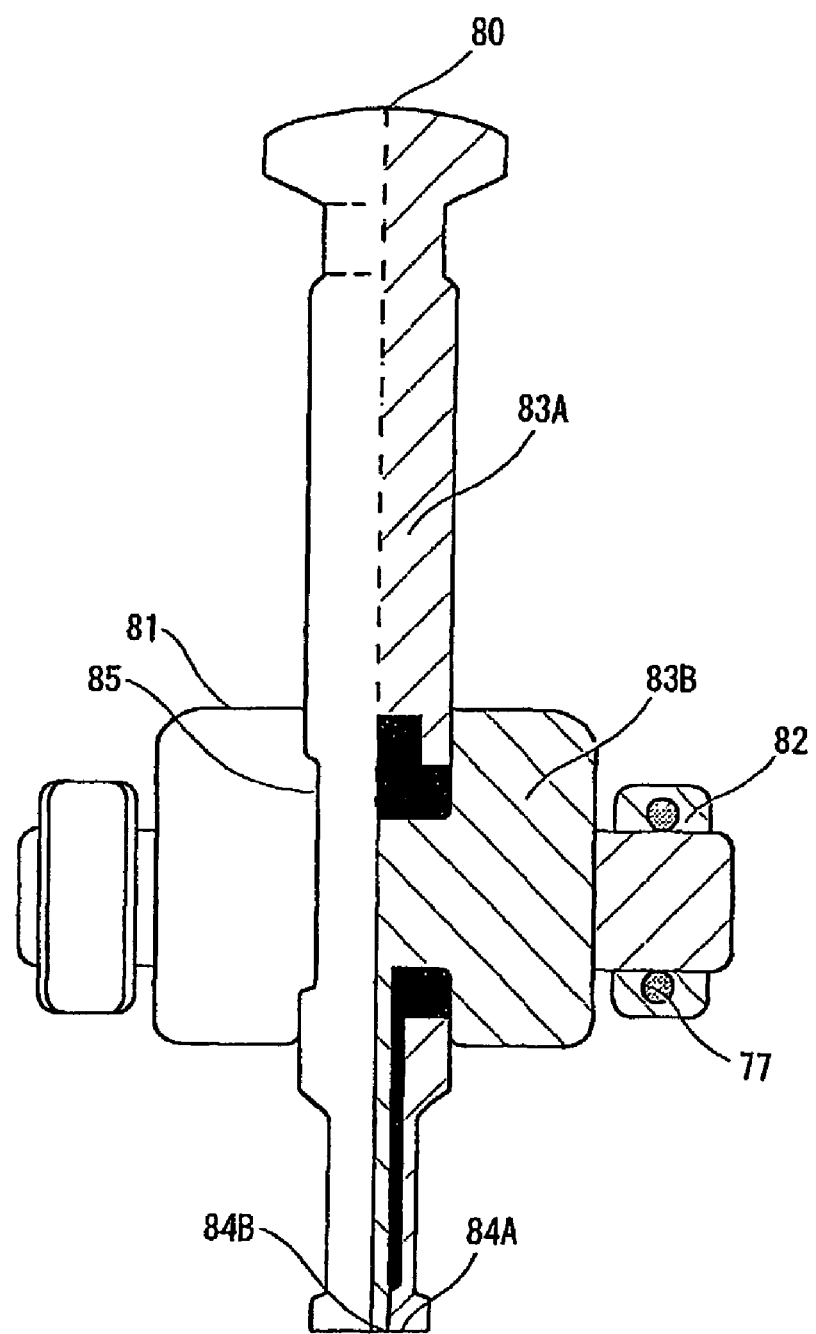
Figure 8:
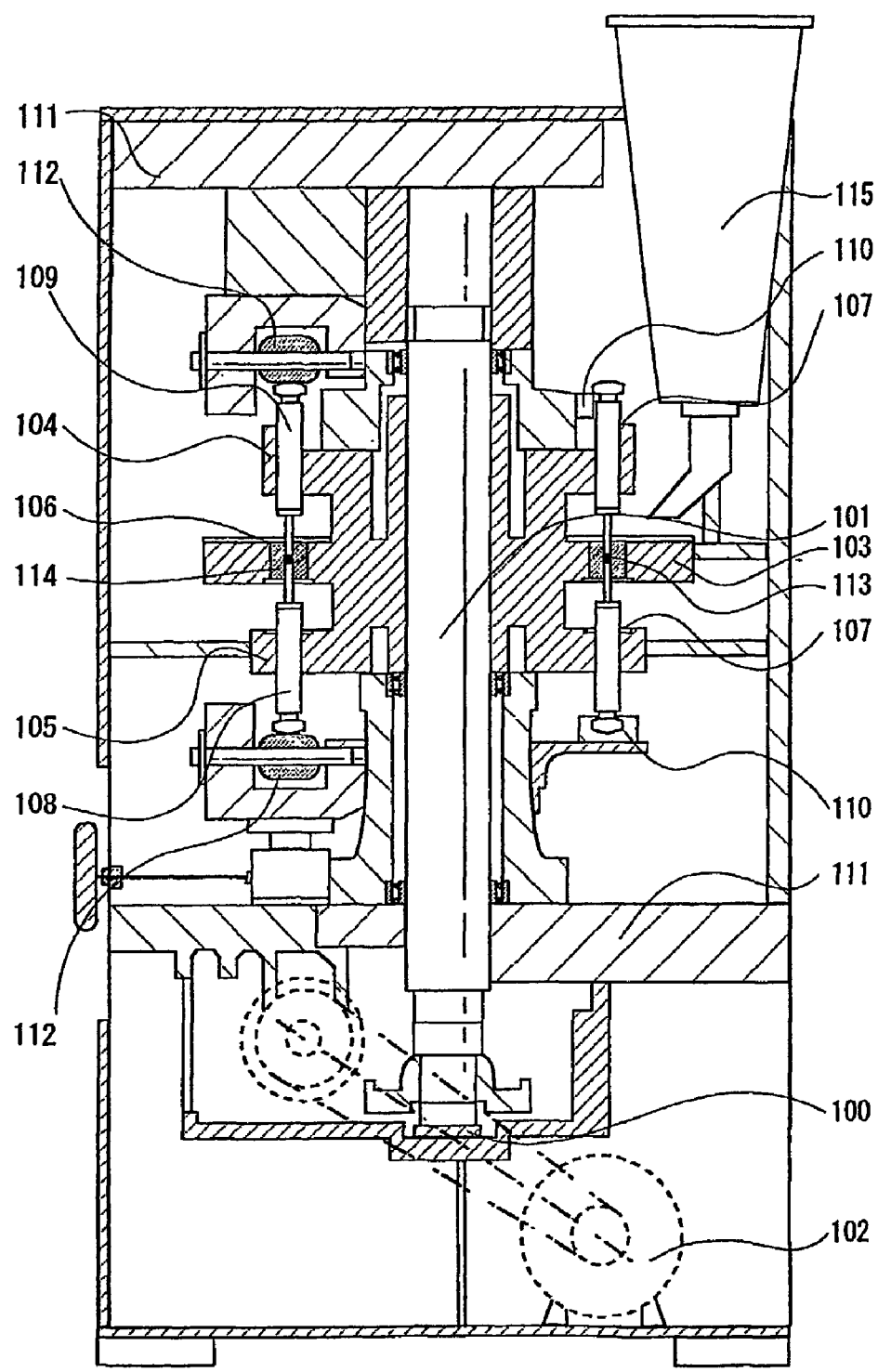
Figure 9:
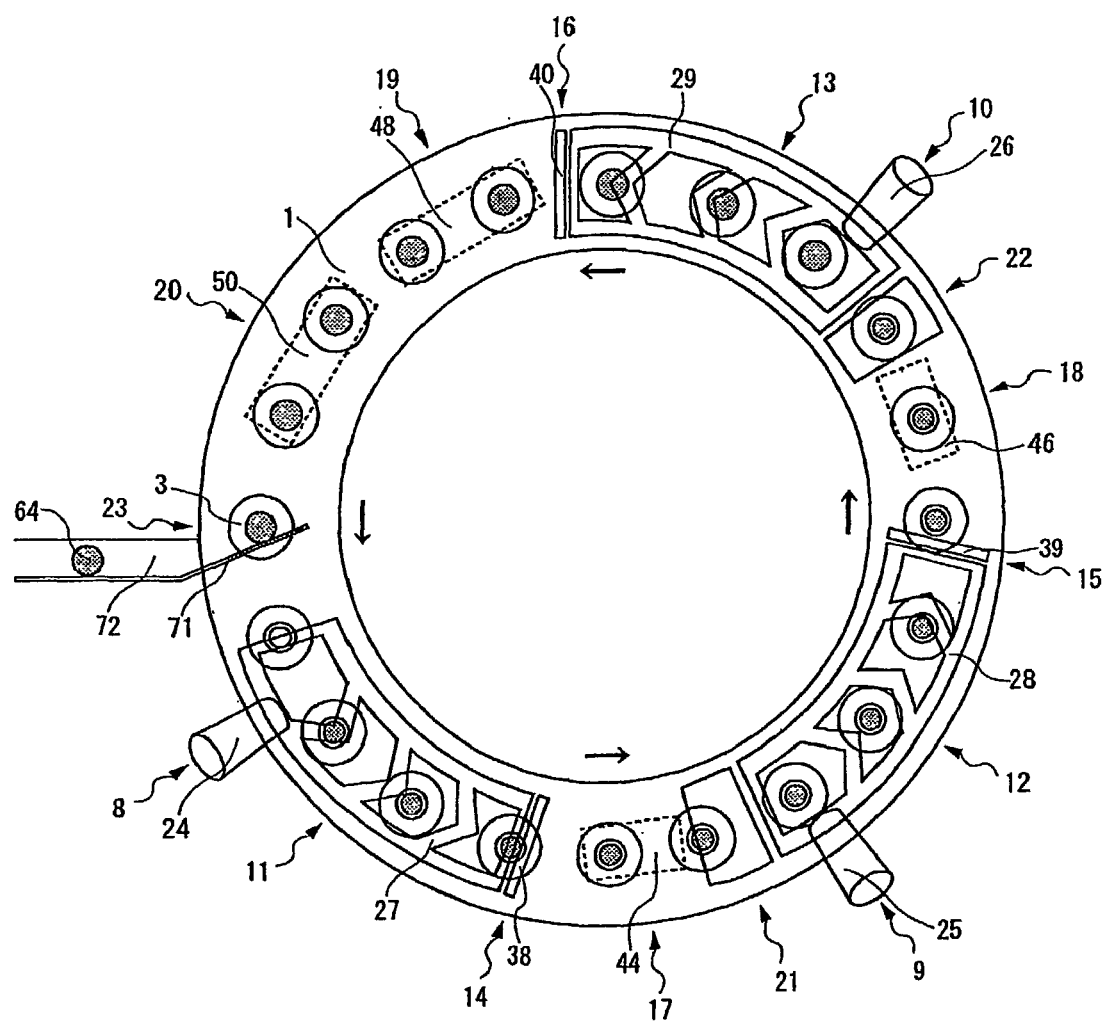
Figure 10:
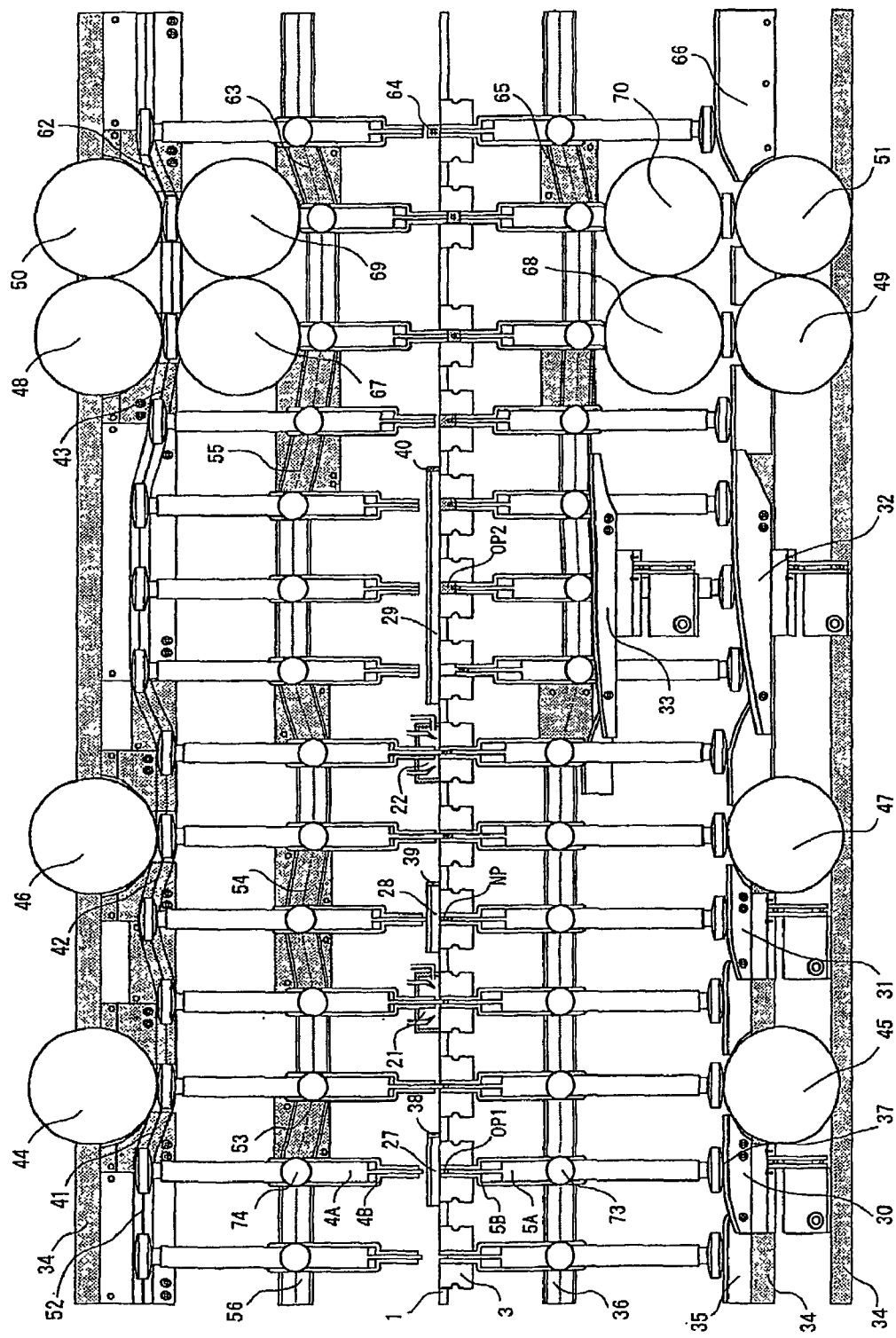
Figure 11:
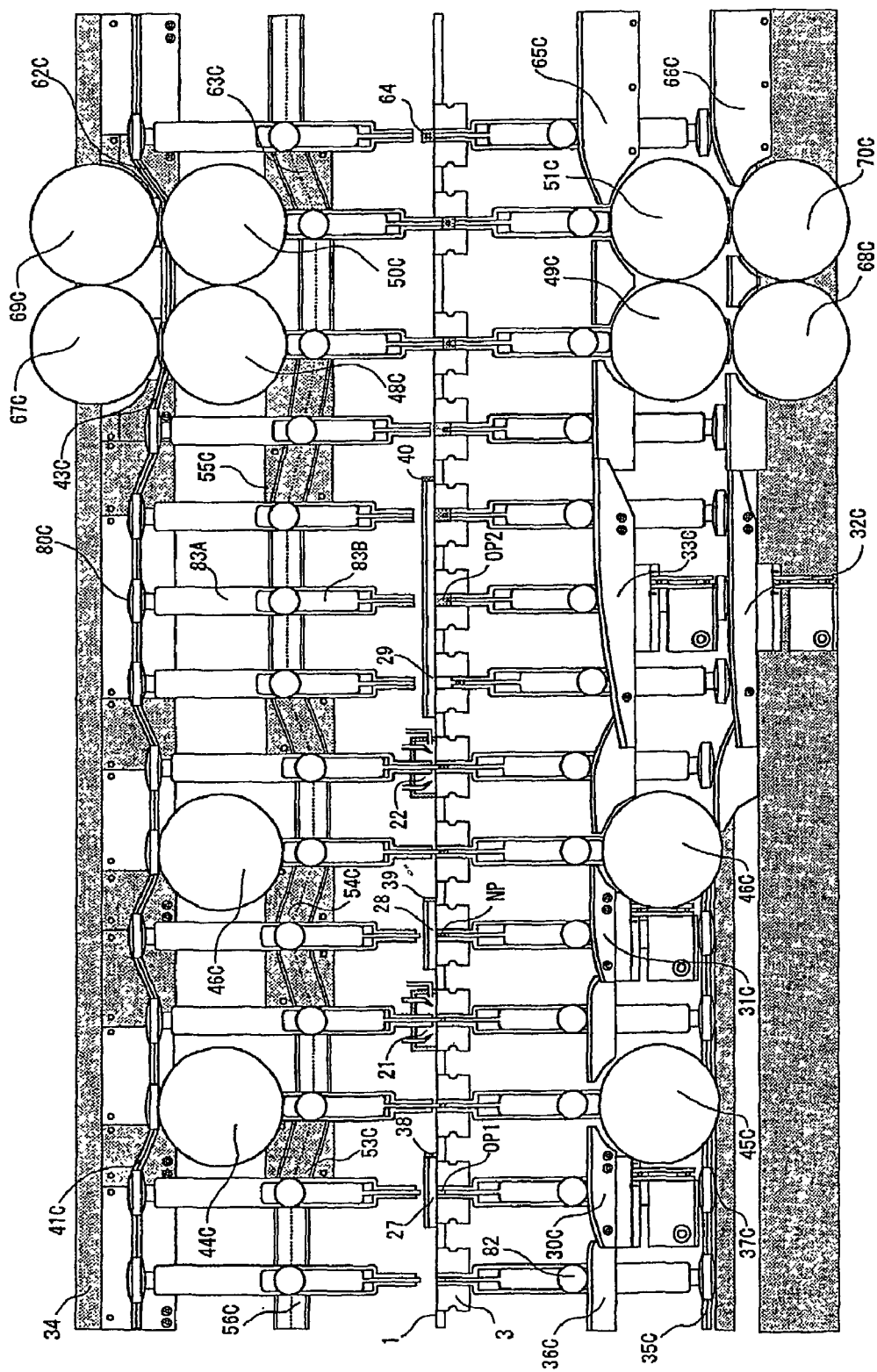
Figure 12:
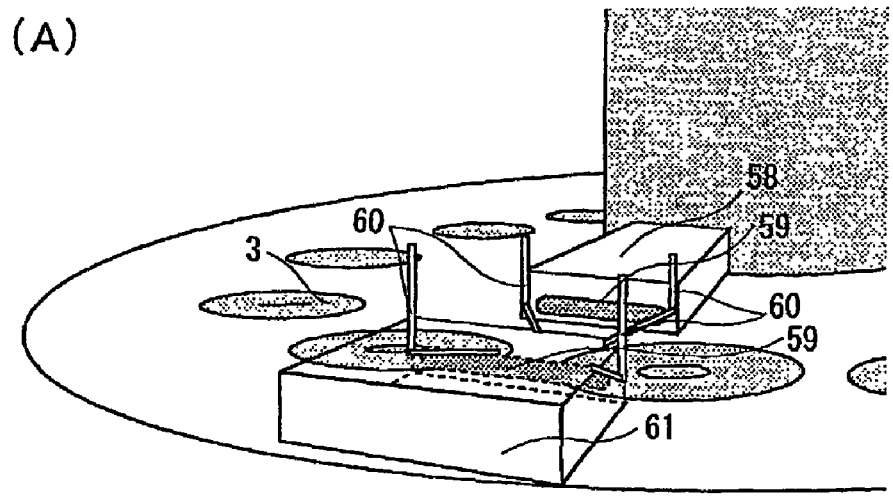
Figure 12:
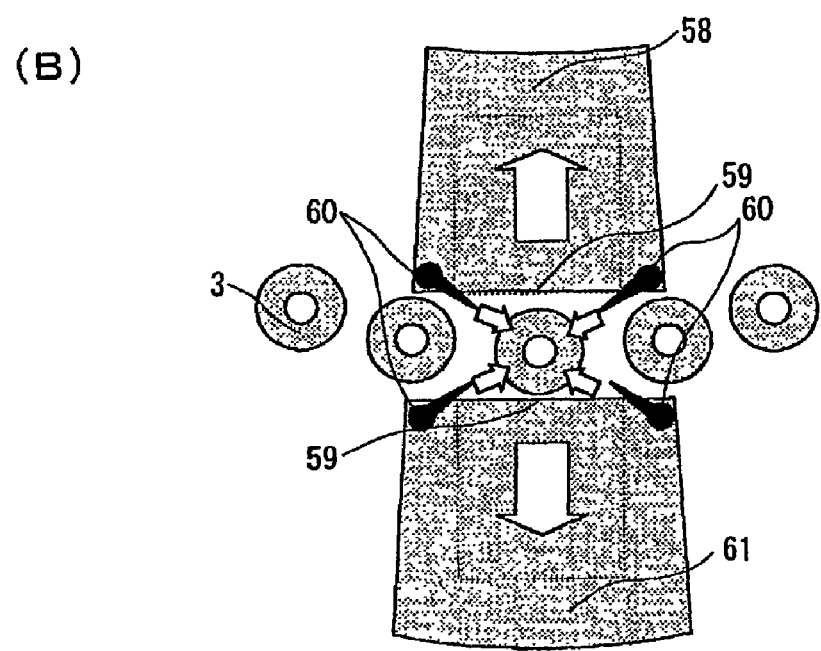
Figure 13:
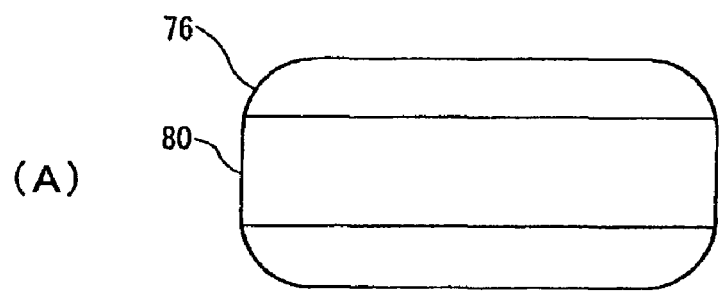
Figure 13:
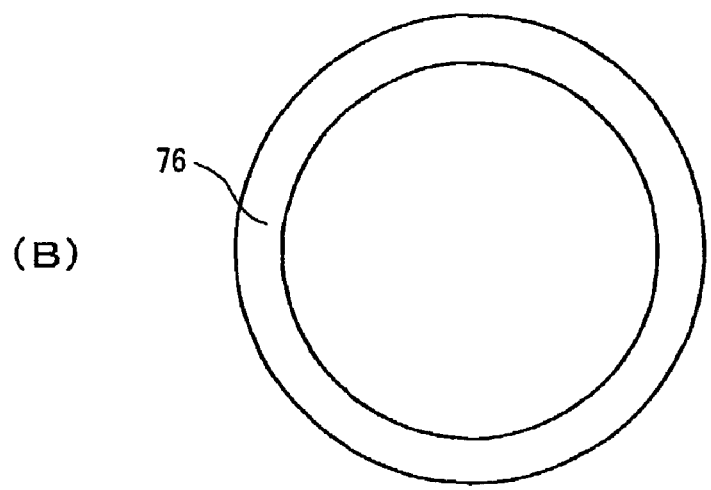
Figure 13:
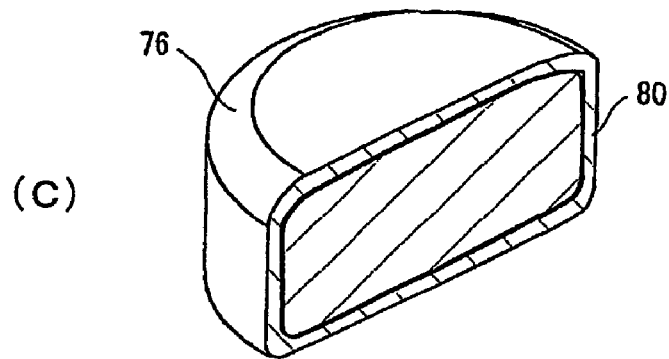
Figure 14:
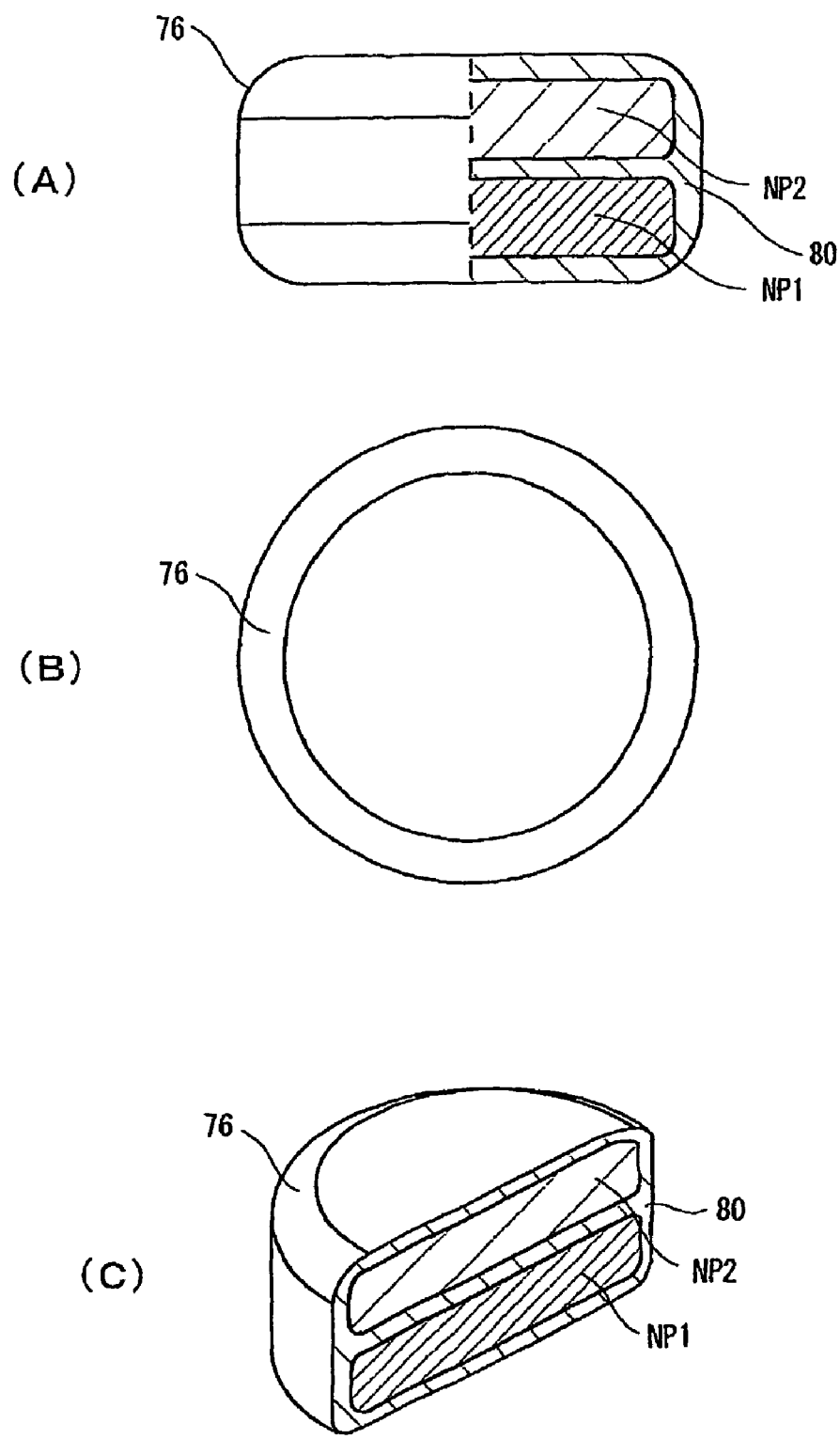

FIG. 1. is an explanatory diagram of the step of a punch tip, showing a first example of a method for the manufacture of a molding with core of the present invention (slanted lines as section are omitted);

FIG. 2. is an explanatory diagram of the step of the punch tip, showing a method for the manufacture of a molding having plural cores of the present invention (slanted lines as section are omitted);

FIG. 3. is an explanatory diagram of the step of the punch tip, showing a second example of the method for the manufacture of a molding with core of the present invention (slanted lines as section are omitted);

FIG. 4. is an explanatory diagram of the step of the punch tip, showing a third example of the method for the manufacture of a molding with core of the present invention (slanted lines as section are omitted);

FIG. 5. is an explanatory diagram of the step of the punch tip, showing a partly altered model of the third example of the method for the manufacture of a molding with core of the present invention (slanted lines as section are omitted);

FIG. 6. shows an example of an upper punch of a punch having a double structure for use in the present invention, (A) being a vertical sectional view (right half) as well as a diagrammatic view (left half), (B) being a side view, which punch corresponds to a double punch of FIG. 10;

FIG. 7. shows, in longitudinal section (right half) and in diagrammatic view (left half), an example of an upper punch of the punch having a double structure for use in the present invention, which punch corresponds to a double punch of FIG. 11;

FIG. 8. is an overall regular cross section of an ordinary rotary compression molding machine, in which a punch, a standing shaft and a hopper are not shown as section;

FIG. 9. is a diagrammatic top plan view of a rotary table in an aspect of a rotary compression molding machine of the present invention;

FIG. 10. is a regular cross section of the rotary table of the rotary compression molding machine of the present invention, showing the step mechanism of upper and lower punches in development, in which an aspect of the apparatus of the present invention is shown, with slanted lines as section omitted;

FIG. 11. is a regular cross section of the rotary table of the rotary compression molding machine of the present invention, showing the step mechanism of the upper and lower punches in development, in which an aspect of the apparatus of the present invention is shown and in which the step modes of the outer and central punches are reversed, with slanted lines as section omitted;

FIG. 12. shows a granular residue removal device of the present invention, with (A) being an overall view of the device and (B) being a top plan view thereof;

FIG. 13. shows a morphology of molding, manufactured by the method and apparatus for manufacturing a molding with core of the present invention, with (A) being a side view thereof, (B) being a top plan view thereof, and (C) being a perspective longitudinal section thereof; and FIG. 14. shows a morphology of a molding having plural cores of the present invention, with (A) being a longitudinal section (right half) as well as a side view (left side), (B) being a top plan view, and (C) being a perspective longitudinal section.

Main reference numerals in diagrams are as follows: 1: rotary table, 3: die, 4A, 83B: upper central punch, 4B, 83A: upper outer punch, 5A: lower central punch, 5B: lower outer punch, 21, 22: granular residue removal unit, 30, 31, 32, 33: reduction device, 35: rail of lower central punch, 36: rail of lower outer punch, 37: bottom of central punch, 41, 42, 43: descent cam of upper central punch, 44,46: upper temporary compression roller, 45, 47: bottom temporary compression roller, 48: preliminary compression roller for upper central punch, 49: preliminary compression roller for lower central punch, 50: main compression roller for upper central punch, 51: main compression roller for lower central punch, 52: rail of upper central punch, 53, 54, 55: descent cam for upper outer punch, 56: rail of upper outer punch, 57 (57A, 57B): granular residue, 62, 63: ascent cam, 65, 66: force rail, 67: preliminary compression roller for upper outer punch, 68: preliminary compression roller for lower outer punch, 69: main compression roller for upper outer punch, 70: main compression roller for lower outer punch, 73: control roller for vertical sliding motion of lower outer punch, 74: control roller for vertical sliding motion of upper outer punch, 78, 80: compression bed for outer punch, 79,81: compression bed for central punch, 82: control roller for vertical sliding motion of central punch, NP: core, OP1: first outer layer, OP2: second outer layer.

DETAILED DESCRIPTION OF THE INVENTION

As described above, the prior art for the manufacture of a molding with core still holds some problems such as productivity problems, expense problems, occasional manufacturing of a molding without core or with plural cores, problems with centering of the core in the process of supplying of the core and with offset of the core due to the centrifugal force of the rotary table, which furthermore cause molding disorders, restrained shape of a core, etc. The method that will solve all these problems at once is not to feed a solid core, molded in advance, but to form at once a molding with core from powder granule, used also as basic molding material for the core. Therefore, the present invention presents a method that allows molding at once the molding with core, or, in other words, a integral molding method, and an apparatus, necessary for it.

According to the present invention there is provided a method for manufacturing a molding with core, the method executed by use of compression molding means, the compression molding means comprising an upper punch and a lower punch which are arranged in the vertical direction of a die, at least the upper punch having a double structure consisting of a central punch and an outer punch surrounding the outer periphery of the central punch, both the central punch and the outer punch being capable of sliding motions as well as compressing operations. Preferably, the lower punch also has such a double structure. The method is a method for manufacturing a molding with core, comprising supply steps of supplying molding material for core and molding material for outer layer, respectively; a compression molding step of compression-molding the molding material for core and/or the molding material for outer layer; and a compression molding step of compression-molding the whole molding with core. More specifically, the method comprises an outer layer supply step 1 of supplying molding material for outer layer, into a space above the lower central punch enclosed by the lower outer punch; a core supply step of supplying molding material for core, into a space above the molding material for outer layer supplied in the preceding step, enclosed by the lower outer punch; an outer layer and core molding step of compression-molding the molding material for outer layer and the molding material for core, supplied in the precedent step; furthermore an outer layer supply step 2 of supplying the molding material for outer layer, into a space in a die above and around the outer layer and a core molding formed in the precedent step; and a whole molding step of compression-molding the outer layer and the core molding and the molding material for outer layer.

In the present invention, an apparatus for execution of the above method can be an apparatus for manufacturing moldings with core, the apparatus being in the form of a rotary compression molding machine having a rotary table which is able to rotate, the rotary table being provided with a die having a die opening, the apparatus having an upper punch and a lower punch which are supported vertically slidably in the vertical direction of the die, the upper punch and the lower punch being moved toward and pressed against each other with the tips of the punches inserted in the die, to thereby perform compressing operations on the molding material filled in the die, wherein at least the upper punch, preferably with the lower punch, has a double structure consisting of a central punch and an outer punch surrounding the outer periphery of the central punch, both the central punch and the outer punch being capable of sliding motions and compressing operations to make up a double punch, and wherein the apparatus comprises means for moving the central punch and the outer punch of the double punch, and means for enabling the compressing operations of the central punch and the outer punch, and wherein the rotary table includes thereon supply sites for molding material for core and molding material for outer layer, respectively, a compression molding site for the molding material for core and/or the molding material for outer layer, and a compression molding site for the whole molding with core. In other words, the present manufacturing apparatus is a rotary compression molding machine, constructed so as to be able to execute a series of steps of the method for manufacturing moldings with core of the present invention. This rotary compression molding machine is easily applicable to manufacture of moldings having plural cores which will be described later.

The present invention also relates to a molding with core, manufactured by the method or apparatus for manufacturing a molding with core of the present invention. The method for manufacturing a molding with core in accordance with the present invention made it possible, when using molding an ingredient with poor moldability, to manufacture a molding with high moldability and high wear resistance without decreasing the amount of the molding material in question and without increasing the size of the finished product. In other words, in the molding with core, manufactured by the method and apparatus of the present invention, molding material with superior moldability are used only or mostly in the compression cover layer, which is an outer layer, while molding material with poor moldability is used mainly in the core and thus the invention succeeded in making smaller in size a molding by decreasing the loadings of excipients and at the same time in improving considerably the moldability and the friability of the molding. Besides, this integral molding method does prevent offset in the positioning of the core and therefore it becomes possible to make the outer layer extremely thin, which also contributes to making the molding smaller in size.

Thus, the molding with core of the present invention have both a core and an outer layer, surrounding the core, which are integrally molded. One aspect provides a molding with core having a core made of an incomplete molding. Another aspect provides a molding with core having an outer layer whose thickness is small and in all its parts is 1 mm or below.

The present invention also relates to provision of a molding with core having plural cores. Beside the many problems, occurring at the manufacturing of a molding having a single core, the manufacturing of a molding having plural cores faced some new problems, such as increased frequency of occurrence of a molding with plural cores or without core, problems of securing unified position of the plural cores, increase in size of the finished molding, etc., all of which are attributable to the manufacturing of a molding with plural cores and oddly shaped a molding with plural cores. The present invention solved at once all these problems and made it possible to provide a molding having plural cores, available in practice, a method for manufacturing the same, and an apparatus used for the execution of the method. In other words, in the method described as the specific preferred method for manufacturing a molding with core, after the core supply step of supplying molding material for core, the molding material for the core or the outer layer is fed in the space enclosed by the lower outer punch and above the previously supplied molding material. Thus, by repeating more than once the step of supplying the molding material for the core or outer layer, a molding having plural cores can be easily manufactured.

The molding having plural cores, manufactured by the method or apparatus for manufacturing the molding with plural cores include plural cores which are distributed vertically with respect to the pressurization surface of the molding. Besides, the method and apparatus for manufacturing a molding having plural cores enable a smooth and fast manufacturing of moldings having plural cores, distributed in specific position. In other words, they provide an aggregate of moldings having plural cores, which is distributed in specific position.

The present invention also relates to a molding with core, containing in the core microcapsular granule (which will be detailed later) such as microcapsules or coated granule that are clusters of particles, which have poor moldability and high brittleness and loose their characteristics, features and functions when destroyed.

In manufacturing a molding with core, containing large amounts of microcapsular granule, it was difficult to secure uniformity of content by amount and prevent increase in size of the finished molding. In the method for manufacturing a molding with core and especially in the method for manufacturing a molding having plural cores of the present invention, a molding was devised that have a structure to apply the microcapsular granule as molding material for core and in that space to insert molding material with superb moldability (ingredients for outer layer). In other words, the method for manufacturing a molding with core of the present invention enables manufacturing of a molding, containing large amounts of microcapsullar granule, which amounts are standardized. The molding in question can prevent increase in size as much as possible, so as to be of size suitable for practical applications.

EXPERIMENTAL DETAILS

Materials and Methods

In this description, the term "molding material" refer to both wet and dry powder granule or other material that can be molded, and the term "powder granule" includes all powder, granule and similar substance.

In a manufacturing method of a molding with core of the present invention and a manufacturing apparatus of moldings with core, the molding material is preferably powder granule.

The method for the manufacture of a molding with core of the present invention is a method for manufacturing a molding with core, the method executed by use of compression molding means, the compression molding means comprising an upper punch and a lower punch which are arranged in the vertical direction of a die, at least the upper punch having a double structure consisting of a central punch and an outer punch surrounding the outer periphery of the central punch, both the central punch and the outer punch being capable of sliding motions as well as compressing operations. Usually the lower punch is also a punch having a double structure a central punch and an outer punch, surrounding the outer periphery of the central punch, both the central punch and the outer punch being capable of sliding motions and pressurization steps. Detailed description on the double structure punche follows in the part of the apparatus for the manufacture of moldings with core of the present invention.

The method for the manufacture of a molding with core of the present invention includes supply steps of supplying molding material for core and molding material for outer layer, respectively; a compression molding step of compression-molding the molding material for core and/or the molding material for outer layer; and a compression molding step of compression-molding the whole molding with core. Preferably the compression molding step of molding material for a core and/or molding material for an outer layer is a temporary compression. Usually the step of supplying the molding material for an outer layer is preformed more than twice.

In such case, depending on the shape of the punch tip, it is necessary or preferable to perform the step of removing of granular residue from the lower outer punch. This will be described in detail later.

A preferred aspect of the method for the manufacture of a molding with core of the present invention is expressed as a method comprising an outer layer supply step 1 of supplying molding material for outer layer, into a space above the lower central punch enclosed by the lower outer punch; a core supply step of supplying molding material for core, into a space above the molding material for outer layer supplied in the preceding step, enclosed by the lower outer punch; an outer layer and core molding step of compression-molding the molding material for outer layer and the molding material for core, supplied in the precedent step; furthermore an outer layer supply step 2 of supplying the molding material for outer layer, into a space in a die above and around the outer layer and core molding formed in the precedent step; and a whole molding step of compression-molding the outer layer and core molding and the molding material for outer layer. The above method is implemented by using compression molding means comprising an upper punch and a lower punch, both the upper and lower punch having a double structure consisting of a central punch and an outer punch surrounding the outer periphery of the central punch, both the central punch and the outer punch being capable of sliding motions as well as compressing operations. This method is basically a method for the manufacture of a molding with core, consisting of the steps described above, but if necessary other steps may be added thereto.

In this method for the manufacture of a molding with core according to the above aspect, when ordinary powder granule is used as molding material, in order to prevent contamination of the powder granule of the outer layer and the powder granule of the core and to make clear distinction between the outer layer part and the core part, it is preferable to perform the outer layer molding step in which the molding material for the outer layer is compression-molded, immediately after the outer layer supplying step 1.

In this method for the manufacture of a molding with core according to the aspect, it is also preferable in the outer layer and core molding step and the outer layer molding step which will be preferably carried out, the compression operation is performed as temporary compression. The molding with core, manufactured in this step is called a temporary molding with core and are included in the group of a molding with core. Also, the compression during the overall molding step could be only main compression, but it is desirable to perform the main compression after preliminary compression (temporary compression). Thus, performing of temporary compression improves the unity of the finished molding and also enables miniaturization of the finished molding with core.

The present invention also relates to the method for the manufacture of a molding having plural cores. By repeating some of the steps of the method for the manufacture of a molding with core according to the aspect, it becomes possible to manufacture easily a molding having plural cores. In other words, by executing an outer layer/core repeated supply step, posterior to the core supply step of supplying the molding material for core, it becomes possible to manufacture easily a molding having plural cores. The outer layer/core repeated supply step includes a core or outer layer supply step repeated more than once, the core or outer layer supply step including supplying the molding material for core or the molding material for outer layer, into a space above the molding materials supplied in the precedent steps, enclosed by the lower outer punch. It is possible to choose whether to feed the molding material for the outer layer or the molding material for the core depending on the need; if, as the outer layer/core repeated supply step, molding material for core is fed, it is possible to manufacture a molding with plural cores, in which two cores are contiguous; also if, as the outer layer/core repeated supply step, molding material for outer layer and molding material for core are fed in the mentioned order, it is possible to manufacture a molding with plural cores, in which two cores are separated by an outer layer. If this step is repeated several times, it becomes possible to manufacture easily a molding with plural cores. Also, in the method for the manufacture of a molding with plural cores of the present invention, when ordinary powder granule is used as molding material, it is preferable to perform the compression molding step every time molding material is fed.

A first example of the optimal aspect of the method for the manufacture of moldings with core of the present invention will be described in detail hereinafter, with reference to FIG. 1. Herein, the compression operation in mid-course is a temporary compression, and the temporary compression operation of molding material for the first outer layer OP1 is performed without omission. Also the expressions such as the molding material for the first outer layer OP1 and the molding material for the second outer layer OP2 are used not to denote different molding material but as a convenient way to distinguish the different parts.

First, as the lower central punch 5A (FIG. 1A) is kept in its lowered position, in the space for the first outer layer 201A, above the lower central punch 5A, which is enclosed by the lower outer punch 5B, the molding material for the first outer layer OP1 is supplied (FIG. 1B); if necessary the lower central punch 5A is raised and after the left-over of the molding material for the first outer layer is discharged out of the die, the upper central punch 4A and the lower central punch 5A move towards each other to perform temporary compression (FIG. 1C) and temporary molding of the first outer layer. (Outer layer molding step)

Next, as the temporary moldings of the first outer layer OP1 is held by the lower central punch (5A) and the lower outer punch (5B), if necessary the lower central layer 5A is lowered and in the space 202A for core above the first outer layer OP1 temporary moldings, which is enclosed by the lower outer punch 5B, the molding material for core NP is supplied (FIG. 1E, F). Then, if necessary the lower central punch 5A is raised, and after the left-over of the molding material for core is discharged out of the die, the upper central punch 4A and the lower central punch 5A move towards each other, to perform temporary compression (FIG. 1G) and temporary molding of the first outer layer and the core. (Outer layer and core molding step)

As the temporary moldings of the first outer layer and the core are held by the lower central punch 5A and the lower outer punch 5B, the lower punch (both the lower central punch 5A and the lower outer punch 5B or the lower outer punch 5B alone) is lowered (FIG. 1I), in the die 3 in the space for the second outer layer 203A, which is above the temporary moldings of the first outer layer and the core and around them, the molding material for the second outer layer OP2 is supplied (FIGS. 1J, 1K). The temporary moldings of the core, which are kept over the first outer layer temporary moldings, is enclosed completely in the molding material for the outer layer and the outer layer temporary moldings (FIG. 1K) and if necessary the left-over of the molding material for the second outer layer OP2 is discharged out of the die 3 (FIG. 1L). However, here the molding material for the second outer layer OP2 can be fed after the lower outer punch 5B is sufficiently lowered beforehand and the temporary molding of the first outer layer and the core are pushed up. After that the upper punch (the upper central punch 4A and the outer central punch 4B) and the lower punch (the lower central punch 5A and the lower outer punch 5B) move towards each other and, if necessary, perform preliminary compression (temporary compression) of the whole moldings, which consists of the first outer layer, the core and the second outer layer, after which perform final main compression (FIG. 1M). (Overall molding step)

FIG. 1N shows the step of taking out the finished moldings.

The tip of the outer punch (6B, 7B) corresponds to the edge 76 on the circumference of the finished molding, shown in FIG. 13 and depending on the shape of the molding it could be flat, but in cases when it is not flat, as shown in FIG. 1, in order to prevent contamination of the molding material for outer layer and the molding material for core, it is preferable to feed an removal step (FIGS. 1D,H) of the molding material residue 57 (57A, 57B) from the surface of the lower outer punch 7B after supplying the first outer layer OP1 or during or after the compression molding (temporary molding) of these molding material, as well as after supplying the core NP or during or after the compression molding (temporary molding) of the first outer layer OP1 and the core NP. This removal step can be performed by shooting and suction of compressed air (the device in FIG. 12) or by brushing, scraper or combination of the above. They are called means for removal of molding material residue.

In the method described above, by performing, after the step of molding of outer layer and core, of the outer layer/core repeated molding step (supply and molding step) performing more than once of the steps of feeding of the molding material for outer layer or the molding material for core and of the compression molding, moldings with plural cores can be easily manufactured. FIG. 2 shows a molding having plural cores, divided by the outer layer, where the first repetition of the above step supplies the molding material for outer layer (for the second outer layer OP2) and the second repetition supplies the molding material for the core (second core NP2). If the supplying of the molding material for core in this step is done just once, the two cores will exist in chain. Besides, FIG. 2 is an example of the case when the tip of the lower outer layer has flat construction and means for removal of molding material residue is not necessary.

As far as the method for the manufacture of moldings having plural cores in the present invention is concerned, the entire step, without skipping the steps of feeding and compression molding each ingredient, can be easily explained as follows.

As the lower central punch is kept in lowered position, in the space for the first outer layer, enclosed by the lower outer punch and above the lower central punch, the molding material for outer layer is supplied and, if necessary, the left-over of the molding material for the first outer layer is discharged out of the die; then the upper central punch and the lower central punch move towards each other and perform compression, thus performing the step of molding of the outer layer molding of the first outer layer. Next, as the lower central punch is kept in lowered position, in the space for the core above the molded first outer punch, enclosed by the lower outer punch, the molding material for core is supplied and, if necessary, the left-over of the molding material for core is discharged out of the die; then the upper central punch and the lower central punch move towards each other and perform compression, thus performing the step of molding of the outer layer and the core molding of the first outer layer and the core. In the same way, as the lower central punch is kept in lowered position, in the space enclosed by the lower outer punch and above the outer layer and the moldings with core, molded in the previous steps, the molding material for outer layer and the molding material for core are fed and, if necessary, the left-over of the molding material is discharged out of the die; then the upper central punch and the lower central punch move towards each other and perform compression, thus performing more than once the outer layer/core repeated molding step molding of the core and the outer layer. Then, as the lower punch is kept in lowered position, above the outer layer and moldings with core and in the space for the final outer layer and around it the molding material for the final outer layer is fed, the moldings with core are completely enclosed in the molding material for outer layer and the outer layer moldings and, if necessary, the left-over of the molding material for final outer layer is discharged out of the die; then the upper punch and the lower punch move towards each other and perform compression, thus performing the step of overall molding.

The present invention method for manufacturing a molding having plural cores can be applied for the manufacture of a molding that contain microcapsules and coated granule, in other words, microcapsule type particles (definition will be given later on) In other words, the microcapsule type particles are used as molding material for core and by using molding material for outer layer in the first repetition of the outer layer/core repeated molding step and microcapsule type particles as molding material for the core in the second repetition of the outer layer/core repeated molding step, the manufacturing of a molding that contain microcapsule type particles can be achieved.

However, when microcapsule type particles are used as molding material for core, necessity to perform compression molding upon feeding of each ingredient is low and at the stages of initial supplying of molding material for outer layer, of initial supplying of microcapsule type particles as well as of second supplying of molding material for outer layer step of compressing makes it even easier for the molding material for outer layer and the microcapsule type particles to mix together and that is why it is preferable to perform temporary compression so that to level the surface.

Incidentally, when the content of microcapsule type particles is low, it is possible to perform the step of supplying of microcapsule type particles just once and skip the process of feeding of outer layer. In other words, in this case even if ingredients with superb moldability are not inserted in the microcapsule type particles in the core, the molding can achieve sufficient moldability and wear resistance.

Next, referring mainly to FIG. 3, detailed description will be made of a second example of the method for the manufacture of moldings with core of the present invention. Here the temporary compression is used as halfway compression. However in this method temporary compression operation of the molding material for first outer layer OP1 cannot be skipped. In exchange, skipping of the temporary compression of the molding material for core NP is possible.

As the lower punch (the lower central punch 5A as well as the lower outer punch 5B) is kept in lowered position (FIG. 3A), the space 201B for first outer layer above the lower punch is filled with the molding material for the first outer layer OP1, if necessary the lower central punch 5A or the lower central punch 5A and the lower outer punch 5B are raised up to a fixed position (FIG. 3B) and the left-over of the molding material for the first outer layer OP1 that has overflowed in the die 3 is discharged. Then the upper punch (the upper central punch 4A as well as the upper outer punch 4B), which is pushed the upper central punch 4A against the side of the lower central punch 5A, and the lower punch (the lower central punch 5A as well as the lower outer punch 5B) move towards each other and by producing compression perform temporary molding of pot-shaped first outer layer (FIG. 3C).

Next, in the space for core 202B inside the temporary moldings of the pot-shaped first outer layer, the molding material for core NP is supplied (FIG. 3E) and, if necessary, the left-over of the molding material for core is discharged. Then, by moving the upper central punch towards the lower punch, the molding material for core NP is subjected to temporary compression and the core NP or the core NP and the first outer layer OP1 are temporarily molded (FIG. 3F).

Then, as the temporary moldings of the first outer layer OP1 and the core NP are supported by the lower punch, if necessary the lower punch is lowered, the molding material for second outer layer is supplied in the space for the second outer layer 203B, which is above the temporary moldings of the first outer layer OP1 and the core NP (FIG. 3H) and then, if necessary, the lower punch is raised up to a fixed position and the left-over of the molding material for the second outer layer OP2 is discharged out of the die 3. Then the upper punch and the lower punch move towards each other, to perform, if necessary, preliminary compression (temporary compression) of the whole moldings, made of the first outer layer, the core and the second outer layer, and finally main compression (FIG. 3I). FIG. 3J shows the step of taking out of the finished moldings.

Furthermore, this method can be applied even if the lower punch is an ordinary punch and not with a double structure. In this case, as shown in FIG. 3B, since the lower central punch cannot be pushed up, there are some minor problems with filling of the molding material and in order to create hollow parts in the flatly filled molding material, using pushed-up upper central punch, in some cases the filling of the molding material on sides is not sufficient. However, when the cores are in small amount, the method can be applied without problems.

In this second example of the method for the manufacture of moldings with core, in order to prevent contamination of the outer layer from the molding material for the core NP, it is preferable, after supplying of the molding material for the core NP or during or after the compression molding (temporary molding) of the core NP (or the core and the first outer layer), to feed an removal step of the residue of molding material for the core 57B, that has stuck on the upper part of the temporary moldings of the first outer layer OP1 at supplying of the molding material for the core NP (FIG. 3F). Furthermore, in FIG. 3F both temporary compression operation and the removal step of the molding material residue are performed simultaneously. This removal step follows the first example of the present manufacturing method.

Next, the third example of this method for the manufacture of moldings with core of the present invention will be explained below, based mainly in FIG. 4. In this method also the temporary compression is used as a halfway compression operation. Furthermore, in this method it is impossible to skip temporary compression operation of the molding material for core NP. The step of compression of the molding material for first outer layer OP1 is optional.

The lower punch (the lower central punch 5A as well as the lower outer punch 5B) is kept in lowered position (FIG. 4A), the molding material for core NP is filled in the space above the lower punch of the die and, if necessary, the lower punch is raised up to a fixed position and the left-over of the molding material for core NP that has overflowed in the die 3 is discharged (FIG. 4B). The upper punch (the upper central punch as well as the upper outer punch 4B) is lowered and inserted in the die; the molding material for core NP is kept in the space among the upper punch, the lower punch and the die (FIG. 4C); the upper outer punch 4B is pushed in the direction of the lower outer punch 5B or the upper central punch 4A is pulled in or both steps are performed and the space for core 202C, enclosed by the upper central punch 4A and upper outer punch 4B, is formed (FIG. 4D); in this space the molding material for core NP is filled by pushing up the lower central punch 5A (FIG. 4E). Then the lower central punch 5A is pushed up into the upper central punch 4A, the upper central punch 4A and the lower central punch 5A move towards each other and produce compression temporarily and thus in the space enclosed by the upper outer punch 4B and under the upper central punch 4A the step of temporary molding of core is performed (FIG. 4F). After that, as the temporary moldings with core is kept on the upper central punch 4A and the upper outer punch 4B, the upper punch is pulled out of the die (FIG. 4G) and at the same time the lower punch is raised against the upper punch and the left-over of the molding material for core NP is discharged (FIGS. 4H, 4I).

Next, in the space for the first outer layer 201C above the lower punch in the die (FIG. 4K), the molding material for first outer layer OP1 is supplied (FIG. 4K) and, if necessary, the left-over of the molding material for first outer layer OP1 is discharged. Then, the lower punch, holding the molding material for first outer layer OP1, is lowered (FIG. 4L), at the same time the upper central punch 4A and the upper outer punch 4B, holding the molding material for core, are lowered and the upper punch is inserted in the die (FIG. 4M). By pushing out the upper central punch 4A in downward direction, the molding material for core is released over the molding material for first outer layer OP1 (FIGS. 4N, 4O). The molding material for second outer layer OP2 is filled (FIG. 4P) above the core temporary moldings as well as in the space for the molding material for second outer layer 203 C around the core temporary moldings (FIG. 4O) and, if necessary, the lower punch is raised up to a fixed position and the left-over of the molding material for second outer layer OP2 is discharged out of the die. After that the upper punch and the lower punch move towards each other and the whole moldings, made of the core, the first outer layer and the second outer layer, is subjected first, if necessary, to a preliminary compression (temporary compression) (FIG. 4Q) and then to a final main compression (FIG. 4R). FIG. 4T shows the step of taking out of the finished moldings.

Furthermore, in the third example for the method for manufacturing of moldings with core of the present invention, as shown in FIG. 5, it is also possible to fill the molding material for core NP in the space above the lower central punch 5A and enclosed by the lower outer punch 5B, then lower the upper punch (the upper central punch 4A as well as the upper outer punch 4B) and move the molding material for core NP from inside the lower outer punch 5B into the upper outer punch 4B.

This method for the manufacture of a molding with core of the present invention can be executed, using the following system: the die has an upper and a lower punches and at least the upper punch, but preferably both the upper and lower punch have double structure, consisting of a central punch and an outer punch that surrounds the outer periphery of the central punch; those central punch and outer punch can perform both sliding and molding steps. Usually, the lower punch, just like the upper punch, has double structure, but as described above in the second example, this method can be executed using ordinary punches too.

Further on in the present invention the rotary compression molding machine is said to be compression molding means, but in general if there are an upper punch, a lower punch and a die, where at least the upper punch has a double structure made up by a central punch and an outer punch that surrounds the outer periphery of the central punch, this method can be executed easily using a hydraulic press. In other words, following the order of steps in the present invention, either the upper and the lower punch or the central and the outer punch are moved manually and/or automatically to a fixed position and after the molding material (molding material for outer layer, molding material for core) is filled, by using a hydraulic press for a series of steps and following the order of steps in the present invention so that to apply pressure form vertically, this method can be easily executed. Furthermore, usually both the lower punch and the upper punch, used in this method, have a double structure. About punches with double structure refers to following explanations as well as FIGS. 6 and 7.

The present invention's method for the manufacture of moldings with core can be executed using the manufacturing apparatus of the present invention, given below.

The present invention's apparatus for the manufacture of moldings with core keeps the generally used traditional rotary compression molding machine, or in other words, the rotary table and it employs a mechanism of rotary molding compression machine where on the plate is set a die with an opening and on the bottom and the top of the die there are bottom and upper punch that can move in both directions and can perform sliding motion; by moving the upper and the lower punch towards each other and pressing the tips of the punches inserted inside the die, the step of compressing of the powder granule inside the die is performed. This apparatus is also constructed so that to be able to perform the series of steps in the present invention method for the manufacture of moldings with core at least the upper punch has a double structure made of a central punch and an outer punch that surrounds the outer periphery of this central punch; in this double structure both the central punch and the outer punch can perform sliding motions as well as compressing operations; the apparatus has means to move the central punch and the outer punch of this double structure and also means to enable the compressing step of the central punch and the outer punch.

In other words, the characteristics of the present invention apparatus for the manufacture of moldings with core are as follows: a rotary compression molding machine device, consisting of a rotary table and a die with an opening on this rotary table, in which there are an upper punch and a lower punch that can move in both directions and can perform sliding motions, performs a compressing step on the molding material, filled in the die, by moving the upper punch and the lower punch towards each other and inserting the tips of the punches in the die; in this rotary compression molding machine at least the upper punch has a double structure made up of a central punch and an outer punch surrounding the outer periphery of this central punch; both the central punch and the outer punch can perform sliding motions as well as compressing operations; the apparatus has means to move the central punch and the outer punch as well as to enable compressing operations of the central punch and the outer punch; on the same rotary table there are a section for supplying of the molding material for core and the molding material for outer layer, a section for compression molding of the molding material for core and/or the molding material for outer layer and a section for compression molding of the whole moldings with core. In this apparatus usually the section for supplying the molding material for outer layer exists on more than two places.

Furthermore, in the present invention apparatus for the manufacture of moldings with core, usually even the lower punch has a double structure, made up of a central punch and an outer punch surrounding the outer periphery of this central punch; both the central punch and the outer punch in this double structure can perform sliding motions as well as compressing operations; the apparatus has means to move the central punch and the outer punch of this double structure as well as to enable compressing operations of the central punch and the outer punch.

Also, usually in the rotary compression molding machine, powder granule is used as molding material and in this case sometimes the apparatus has a device for removing the powder granule residue, left on the lower outer punch or on the molding, due to the shape of the punch tip.

Preferable form of the present invention apparatus for the manufacture of moldings with core is a rotary compression molding machine with the following characteristics: both the upper and the lower punch have double structure, made of a central punch and an outer punch that surrounds the outer periphery of the central punch; both the central punch and the outer punch can perform sliding motions as well as compressing operations; the apparatus has means to move the central punch and the outer punch of the double structure as well as means to enable compressing operations of the central punch and the outer punch; the apparatus has a section for first supplying of molding material in the space enclosed by the outer punch, a section for first compression molding of the molding material, using the upper central punch and the lower central punch, a section for second supplying of molding material in the space enclosed by the outer punch, a section for second compression molding of the molding material, using the upper central punch and the lower central punch, a section for supplying in the space inside the die of the final molding material and a section for compression molding of the whole moldings, using the upper and the lower central and outer punch.

In order to provide more detailed explanation of the present invention apparatus for the manufacture of moldings with core, first the traditional rotary compression molding machine will be explained.

The rotary compression molding machine, as shown in FIG. 8, if for example is a shaft-operated device, is constructed as follows: in the central part of the main frame ill a standing shaft 101 is placed, supported by a bearing 100; the revolving operating power is transmitted to the shaft by a motor 102 and near the shaft a rotary table 103, divided into two functional parts, is fixed. Furthermore, in order to press the rotary table from up and bottom, above and under the rotary table respectively a holding section for an upper punch 104, enabling vertical sliding motion of the upper punch and a holding section for the lower punch 105, enabling vertical sliding motion of the lower punch are set. On the rotary table 103 multiple die units with same circumference as the die opening 106 in order to correspond to ability of the die 114 to be attached and removed are set. In the holding section for upper punch 104 and the holding section for the lower punch 105, punch-holding openings 107, supporting sliding motions of the upper punch and the lower punch, are drilled. In this rotary table, in order to distribute the lower punch 108, the upper punch 109 and the die 114 so that their centerlines coincide, a punch holder opening 107 and a die opening 106 respectively are drilled. A rail 110 is set so as to correspond to parts where trajectories of the upper punch 109 and the lower punch 108 touch; this rail is constructed so as to connect with each cam and to move vertically. In the die 114, the opening 113 goes all the way through, in order to insert the tips of the upper punch 109 and the lower punch 108. Furthermore, in FIG. 8 reference numerals 112 and 115 denote a compression roller and a hopper, respectively.

There are also rotary compression molding machines, where the revolving operating power is supplied not by a shaft, but by a gear on a rotary table. They could be external gear operated (external gear type) and internal gear operated (internal gear type).

Next follows an explanation of the punches with double structure and the parts, attached to them.

The two-layer punch, used in the present invention, consists of a central punch and an outer punch that surrounds the outer periphery of this central punch, where the outward form of the outer punch is almost the same as the inside form of die and the outward form of the central punch is almost the same as the outward form of the core and the inside form of the outer punch. Furthermore, both the central punch and the outer punch can perform sliding motions as well as compressing operations. When the sliding part that connects both punches is removed, basically the central punch and the outer punch can perform sliding motions separately.

One example is a punch, corresponding to FIG. 10, which has construction as shown in FIG. 6 a central punch 4A, an outer punch 4B, an outer punch compressing bed 78, a central punch compressing bed 79 and a control roller for vertical sliding motion of the outer punch 74. In the compressing step, compression of the central part of tablets with large compressing area is performed by pressing of the central punch compressing bed 79 into the compression roller (44, 46, 48, 50 in FIG. 10) and compression of the outer part of tablets is performed by pressing of the outer punch compression bed 78 into the compression roll (67, 69 in FIG. 10). Thus compression operations of the central punch and the outer punch are enabled.

Furthermore, the vertical sliding motion of the central punch is controlled according to the usual method by the rail of the central punch and the central punch bottom part 37 (identical to the central punch compression bed 79), but in order to enable the vertical sliding motion of the outer punch, a vertical sliding motion control roller 74, directly touching the outer punch rail, is set. Preferably in this roller multiple bearings 77 are placed, so that the roller could rotate and enable smooth vertical sliding motion of the outer punch.

Here, by placing the vertical sliding motion control roller 74 on the outer side of the outer layer compressing bed 78 and separating the vertical sliding motion control roller 74 from the outer layer compressing bed 78, during pressurization compression the roller pressurizes only in the outer layer compressing bed 78 and does not apply direct pressurization on the vertical sliding motion control roller 74 so that the bearings 77 inside the vertical sliding motion control roller 74 are protected from damage. In the compression operation, even stronger pressurization can be applied on the side of the central punch towards the outer punch and thus it is possible to transmit effectively pressure from the compression roll to the molding material.

Furthermore, by separating vertically the central punch and the compression roller contact part of the outer punch (the outer punch compression bed 78 and the central punch compression bed 79) interference between compression rollers for the central punch and for the outer punch is prevented.

FIG. 6 shows the upper punch, but the same is true for the lower punch also, when a punch with double structure is used. When the lower punch is also with double structure, its differences from the upper punch are as follows: the tip of the lower punch that is inserted in the die is longer and in order to differentiate movements of the upper and the lower punches, parts that regulate movements of the punch (a space inside a die, etc) are different.

Another two-layer punch that can be used in the present invention, as shown in FIG. 11, is a punch that controls the movement of the central and the outer punches in reverse. In other words, this punch controls the movement of the central punch by a vertical sliding motion control roller and a rail and the movement of the outer punch by a punch bottom part (the same part as the outer punch compression bed 80) and a rail. This punch is also characterized, as shown in FIG. 7, by an opening in the outer punch (outer punch opening section 85), from which the central punch compression bed 81 as well as the central punch vertical sliding motion control roller 82, which are a one body with the central punch, protrude. As far as this punch is concerned, all details except for the reverse control of the movements of the central punch and the outer punch are the same as the details in the punch shown in FIG. 6., so explanations are omitted. Furthermore, since in the outer punch an opening section is set, troubles with friction due to adherence and mixing of powder granule are feared to occur so this punch is not considered to be of preferable construction. (Explanation of some of reference numerals is omitted)

Next follows a detailed explanation of each section and its steps of the apparatus, corresponding to the first example of the present invention method for the manufacture of moldings with core (FIG. 1), presented as the present invention apparatus for the manufacture of moldings with core or, in other words, as a rotary compression molding machine. Explanation is based mainly in FIGS. 9 and 10 and, if necessary, in FIG. 1. Powder granule is used as molding material in this form of the apparatus.

On top of a rotary table 1, following the direction of revolving, as shown in FIG. 9, powder granule supplying sections 8, 9, 10, powder granule filling sections 11, 12, 13, powder granule leveling sections 14, 15, 16, compression molding sections 17, 18, 19, 20, powder granule residue removal sections 21, 22 and a molding taking-out section 23, are set.

If each mechanism has to be explained separately, depending on the kind of powder granule to be supplied, the powder granule supplying sections (8, 9, 10 in FIG. 9) are divided into the section 8 for supplying of powder granule for the first outer layer OP1, the section 9 for supplying of powder granule for the core NP and the section 10 for supplying of powder granule for the second outer layer OP2; supplying of powder granule is performed by natural falling from a hopper 24, 25, 26 that has filled each type of powder granule or by a fixed amount supplying mechanism (not shown).

Each type of powder granule, supplied by the section for supplying of powder granule, are next sent to the section for filling powder granule (11, 12, 13 in FIG. 9). The section for filling of powder granule is a section for supplying of powder granule, used respectively for the first outer layer OP1, the core NP and the second outer layer OP2, into the space for the first outer layer 201A, the space for core 202A and the space for second outer layer 203A (see FIG. 1). There, the different types of powder granule, supplied by the section for supplying of core bodies, are maintained in fixed amount in an open feeding-plate 27, 28, 29, which performs both the functions to store the powder granule and to supply the powder granule. Then, by lowering the lower central punch 5A, using lowering devices 30, 31, 32 that are set on the frame 34 or by lowering the lower outer punch 5B, using a lowering device 33 that is set on the lower outer punch rail 36, the powder granule stored in the open feeding-plate 27, 28, 29 is brought into the space for the first outer layer 201A, the space for the core 202A and the space for the second outer layer 203A (see FIG. 1).

In details, the step of filling powder granule for the first outer layer is performed in the first open feeding-plate 27 on the rotary table 1 by lowering the lower central punch 5A (FIGS. 1A and 1B). Here the lower outer punch 5B, using the lower punch vertical sliding motion control roller 73, puts into motion the lower outer punch rail 36, which is set so that to put on same level the lower outer punch tip and the rotary table 1; thus the lower outer punch maintains the same height as the rotary table. On the other hand, the lower central punch 5A connects the lower central punch rail 35, set on the frame 34, with the rotary table step and is put into motion by the lower central punch bottom part 37 (part which is essentially identical with the central punch compression bed 79, shown in FIG. 6); furthermore, using the first central punch lowering device 30, set on the lower central punch rail 35, it regulates the mechanism in fixed position. Thus powder granule for the first outer layer OP1 is brought into the space for the first outer layer 201A, which is above the lower central punch 5A and enclosed by the lower outer punch 5B.

Next, the step of filling the powder granule for core NP is performed in the second open feeding shoe 28 on the rotary table 1, in a way similar to that of the first outer layer OP1 by lowering the lower central punch 5A only (FIGS. 1E and 1F).

Here, using the lower outer punch vertical sliding motion control roller 73, the lower outer punch 5B puts into motion the lower outer punch rail 36, which is set in order to level the lower outer punch 5B tip with the rotary table 1, and thus maintains its height with the rotary table at a fixed level. On the other hand, the lower central punch 5A, which maintained the first outer layer temporary moldings on its upper edge 7A, puts into motion the lower central punch rail 35, set on the frame 34, using the lower central punch bottom 37 that moves connected with the step of the rotary table. Furthermore the lower central punch 5A lowers the lower central punch rail 35, using the second central punch lowering device 31, set on the lower central punch rail 35. Thus the powder granule for core NP is brought into the space for the core 202A, enclosed by the lower outer punch 5B and above the first outer layer temporary moldings.

Next, the step of filling the powder granule for the second outer layer OP2 is performed in the third open feed shoe 29 on the rotary table 1, by lowering both the lower central punch 5B, that still holds the temporary molded first outer layer OP1 and the core NP, and the lower outer punch 5B or only the lower outer punch 5B (FIGS. 1I and 1J). Here the lower outer punch 5B is lowered using the lowering device for lower outer punch 33, set on the lower outer punch rail 36. Further, the lower central punch 5A, using the lower central punch bottom 37, which moves connected with the step of the rotary table, puts into motion the lower central punch rail 35 and then lowers it, using the third central punch lowering device 32, set on the lower central punch rail 35. Thus, by lowering both the lower central punch 5A and the lower outer punch 5B, or the lower outer punch 5B only, the powder granule for the second outer layer OP2 is brought into the space for the second outer layer 203A, in the die 3 above first the outer layer OP1 and the core NP temporary moldings and around them.

In FIG. 10 the third open feed shoe 29 is printed in bigger format than the other open feed shoes, but this is in order to show the details more explicitly. Furthermore, instead of the open feed shoe, a stirring feed shoe, which fills the powder granule into the die by force using stirring blades, can be used. (The stirring feed shoe is set at the same place as the open feed shoe; not shown).

Next, the die, filled with the powder granule in the powder granule filling section, and the punches enter in the powder granule leveling section (14, 15, 16 in FIG. 9). The powder granule leveling section controls in a fixed amount the powder granule for the first outer layer OP1, the powder granule for the core NP and the powder granule for the second outer layer OP2, supplied as described above. In other words, using the lower outer punch rail 36 and the lower central punch rail 35, this section raises the lower central punch 5A or both the lower central punch 5A and the lower outer punch 5B to a fixed position and thus, using the leveling boards 38, 39, 40, files through the left-over of the powder granule that has overflowed from the appointed space and removes it.

Speaking in details, the leveling of the powder granule for the first outer layer OP1 is performed with the leveling board 38, which is attached to the first open feed shoe 27 on the revolving board 1. Here, as the tip of the lower outer punch 5B is on the same plane with the rotary table, by raising the lower central punch 5A to a fixed position, the left-over of the powder granule for the first outer layer OP1 that are filled in the space for the first outer layer 201A is forced to overflow out of this space. Next, the powder granule for the first outer layer OP1, that have overflowed, are filed through by the leveling board 38, attached to the open feed shoe 27 and the filled powder granule for the first outer layer OP1 are leveled to a fixed amount. (Before and after FIG. 1B)

Next, the leveling of the powder granule for the core NP, is performed, same as in case of the first outer layer, with the leveling board 39, which is attached to the second open feed shoe 28 on the rotary table 1. Here, as the tip of the lower outer punch 5B is on the same plane with the rotary table, by raising the lower central punch 5A to a fixed position, the left-over of the powder granule for the core NP, that are filled in the space for core 202A, is forced to overflow out of this space. Next, the powder granule for the core NP, that has overflowed, is filed through by the leveling board 39, attached to the second open shoe 28 and thus the filled powder granule for the core NP is leveled to a fixed amount (before and after FIG. 1F).

Then, the leveling of the powder granule for the second outer layer OP2 is performed, same as in case of the first outer layer and the core, by the leveling board 40, attached to the third open feed shoe 29 on rotary table 1. Here by raising the lower central punch 5A or both the lower central punch 5A and the lower outer punch 5B to a fixed position, the first outer layer and the core NP temporary moldings, held by the lower central punch 5A and the lower outer punch 5B, are pushed up into the powder granule for the second outer layer OP2, which are supplied in the opening of the die 3 and the left-over of the powder granule for the second outer layer OP2 are forced to overflow. Then the powder granule for the second outer layer OP2, that has overflowed, is filed through by the leveling board 40, attached to the third open feed shoe 29, and the filled powder granule for the second outer layer OP2 is leveled to a fixed amount (after FIG. 1K).

Next, the die, filled with the fixed amount of powder granule, leveled in the powder granule leveling section, and the punches enter the compression molding sections (17, 18, 19, 20 in FIG. 9). The compression molding section performs temporary or main compression of the powder granule for the first outer layer OP1, the powder granule for core NP and the powder granule for the second outer layer OP2 any of them separately or in combination (including the temporary moldings), which are supplied in the fixed parts and the fixed amounts, using the compression roller (44 to 51, 67 to 70), held by the frame 34.

Speaking in details, the temporary compression of the powder granule for the first outer layer OP1 or of the first outer layer OP1 temporary moldings and the powder granule for the core NP is performed by pressuring action of the upper central punch 4A and the lower central punch 5A. Here, the upper central punch 4A is lowered by the upper central punch lowering cam 41, 42, set on the upper central punch rail 52, preferably at the same time the upper outer punch 4B is lowered to a fixed position by the upper outer punch lowering cam 53, 54, set on the upper outer punch rail 56 and the tip of the upper central punch A4 is inserted in the space, enclosed by the lower central punch 5A and the lower outer punch 5B, in the die 3. Thus, by binding vertically the powder granule for the first outer layer OP1 or the temporary moldings for the first outer layer OP1 and the powder granule for the core NP, filled in the appointed space and pressing them using the upper temporary compression rollers 44, 46 and the bottom temporary compression rollers 45, 47, step of molding of temporary compressed materials is performed. (FIG. 1C, FIG. 1G) Furthermore, it is possible, although not preferable, to skip the first section for moldings by temporary compression of the powder granule for the first outer layer OP1.

Next, a preliminary compression (temporary compression) of the temporary moldings of the first outer layer OP1 and the core NP and the powder granule for the second outer layer OP2 is performed, using the compression action of the upper central punch 4A and the upper outer punch 4B (upper punch), and the lower central punch 5A and the lower outer punch 5B (lower punch) In order to insert the upper central punch 4A and the upper outer punch 4B into the die 3, the upper central punch 4A and the upper outer punch 4B are lowered to an appointed position by the upper central punch lowering cam 43, set on the upper central punch rail 52 as well as by the upper outer punch lowering cam 55, set on the upper outer punch rail 56, then their tips are inserted in the die 3, the temporary moldings of the first outer layer OP1 and of the core NP and the powder granule for the second outer layer OP2 are bound vertically and the preliminary compression molding is performed, using the preliminary compression roller for upper central punch 48, the preliminary compression roller for the upper outer punch 67, the preliminary compression roller for the lower central punch 49 and the preliminary compression roller for the lower outer punch 68.

The main compression that follows the preliminary compression (temporary compression) is a compression molding step of the temporarily compressed moldings, using the main molding roller for the upper central punch 50, the main compression roller for the upper outer punch 69, the main compression roller for the lower central punch 51 and the main compression roller for the lower outer punch 70. (FIG. 1M) Furthermore, it is possible, although not preferable, to skip the section for preliminary compression of the temporary moldings of the first outer layer OP1 and the core NP and the powder granule for the second outer layer OP2, and to perform only this main compression operation.

Next, the section for removal of powder granule residue (21, 22 in FIG. 9), is in or immediately after the section for temporary compression of the powder granule for the first outer layer OP1 or the core NP. As shown in FIG. 1, during the step of temporary molding or immediately after it, as the tip of the lower outer punch 5B is on the same plane as the rotary table 1 and, preferably, the upper central punch 4A is inserted in the space inside the lower outer punch 5B, the powder granule for the first outer layer OP1 57A and the powder granule for the core NP 57B, that have remained on the surface of the upper edge of the lower outer layer 7B, are removed by shooting of air under pressure and suction.

Speaking in details, the upper edge surface 7B of the lower outer punch 5B, shown in FIG. 1 fits with the edge of the circumference 76 (not right angle) of the completed moldings, shown in FIG. 13 and in this part the powder granule residue 57 (57A, 57B) is left. This powder granule residue 57 cannot be leveled and removed by the open feed shoe, set on the rotary table 1 and by the leveling board 38, 39 of the stirring feed shoe and when the powder granule residue is not removed, contamination between the powder granule for the first outer layer OP1 and the powder granule for the core NP, as well as contamination between the powder granule for the core NP and the powder granule for the second outer layer OP2, is feared. For this reason after temporary compression operation, the powder granule residue 57 (57A, 57B) is removed by the first powder granule residue removal unit 21 and the second powder granule residue removal unit 22, set on the rotary table 1 (FIGS. 1D and 1H). The mechanism for removal of powder granule residue, for example as shown in FIG. 12, is placed on the rotary table parallel to the direction of revolving, so as to press on both sides the die and the punches, and consists of a nozzle for shooting of air under pressure 60, shooting air under pressure from four sides into surface of the die and a suction box 58, 61 with a suction opening 59, sucking powder granule residue. The nozzle for shooting of air under pressure 60 shoots towards the punches and the die from four sides and by the suction opening 59, which is placed close to the die, sucks the powder granule residue, so that the powder granule residue 57 is not scattered outside but is totally removed. This device for removal of powder granule residue is the device for removal of powder granule residue of the present invention. Furthermore, in some cases this unit for removal of powder granule residue could be omitted. Especially when moldings with flat surface is manufactured, since the surface of the outer punch is also flat, the unit for removal of powder granule residue is not necessary. Finally the obtained moldings are sent to the unit for taking out of products (23 in FIG. 9) to be discharged out of the molding machine. The unit for taking out of products is placed so as to take out the ready products, using the lower central punch 5A and the lower outer punch 5B, which rise and thus push up the products and the scraper 71, which leads them to the chute 72.

Speaking in details, by raising the upper central punch 4A and the upper outer punch 4B, using the upper central punch raising cam 62 and the upper outer punch raising cam 63 and putting them in a position so as to follow slanted surface, the tips of these punches are taken out of the die 3; then, using the lower central punch push up rail 66 and the lower outer punch push up rail 65, the lower central punch 5A and the lower outer punch 5B are pushed up and the molding 64 in the die 3 are pushed completely out of the die 3. Furthermore, in order to make the step of taking out of moldings easier, it is preferable to keep the surface of the tip of the lower outer punch 5B so as to be on the same level with the rotary table surface and lower central punch 5A to be pushed up a little bit higher than it (FIG. 1N). In order to be discharged out of the rotary table 1, the pushed out molding 64 are taken by the scraper 71 and are led into the chute 72. Thus the products are taken out.

In FIG. 10, in the apparatus of the present invention, the following devices are shown as means to put into motion the central punch and the outer punch: a rail (a lower outer punch rail 36, a lower central punch rail 35, an upper outer punch rail 56, an upper central punch rail 52), a declining mechanism (a first central punch declining mechanism 30, a second central punch declining mechanism 31, a third central punch declining mechanism 32, a declining mechanism for lower punch 33), a raising cam (an upper central punch raising cam 62, an upper outer punch raising cam 63), a lowering cam (an upper central punch lowering cam 41, 42, 43, an upper outer punch lowering cam 53, 54, 55), a push up rail (a lower central punch push up rail 66, a lower outer layer push up rail 65), as well as a vertical sliding motion control roller (a lower outer punch vertical motion control roller 73, a upper outer punch vertical sliding motion control roller 74), a central punch bottom unit 37 and a bearing 77. Furthermore, as means that enable the compression operations of the central punch and the outer punch, the following devices are shown: a compression roller (an upper temporary compression roller 44, 46, a bottom temporary compression roller 45, 47, a preliminary compression roller for upper central punch 48, a preliminary compression roller for upper outer punch 67, a preliminary compression roller for lower central punch 49, a preliminary compression roller for lower outer punch 68, a main compression roller for upper central punch 50, a main compression roller for upper outer punch 69, a main compression roller for lower central punch 51, a main compression roller for lower outer punch 70) as well as an outer punch compression bed 78 and a central punch compression bed 79, shown in FIG. 6. Still more, these include factors not only of the apparatus itself, but also factors of the punches.

Among the means that put into motion the central and the outer punches and enable the compression operations of the central and the outer punches, as already was explained in the part concerning the punches, besides the methods, shown in FIG. 10, to control the movement of the outer punch by the vertical sliding motion control roller and the rail, and the movement of the central punch by the central punch bottom unit and the rail (corresponding to the punch in FIG. 6), methods, shown in FIG. 11, to control the movement of the central punch by a vertical sliding motion control roller and a rail, and the movements of the outer layer by a punch bottom unit and a rail are also possible. As previously described and shown in FIG. 7, for execution of the latter methods it is necessary to set an opening section in the outer punch so they could cause troubles such as friction due to mixing of the powder granule, and therefore the former methods are considered as preferable.

Furthermore, FIG. 11, just like FIG. 10, corresponds to the first example (FIG. 1) of the present invention method for manufacturing moldings with core. The movement of the punches here is controlled in a reverse way to that of FIG. 10 and therefore there are some parts with different names, but the basic mechanisms are the same as in FIG. 10, so the explanation of names and symbols is omitted. The symbols in FIG. 11 concerning the parts with different names from the ones in FIG. 10, due to reverse control, have a C attached to the symbol of the corresponding parts in FIG. 10.

In case of manufacturing of moldings having plural cores, using the apparatus for the manufacture of moldings with core of the present invention, depending on the number of cores and of outer layers that separate one core from the other, on the same rotary table are fed sections which perform moldings from step of supplying of cores or outer layers, as well as a unit for removal of powder granule residue. In other words, on the rotary table in FIG. 9, together with the unit for removal of powder granule residue, necessary number of sections, performing molding from step of supplying cores, are fed.

The apparatus, used in the second example (FIG. 3) of the present invention's method for the manufacture of moldings with core, is basically the same as the apparatus, used in the first example that was explained in details. The differences are in the means for putting into motion the punches and in the means for compression, as well as in the fact that in the second example the unit for removal of powder granule residue is only one. Furthermore, the apparatus used in the third example of the present invention's method for the manufacture of moldings with core, is the same as the apparatus, used in the first and the second example.

Up to here explanations have been provided, concerning the present invention's method for the manufacture of moldings with core and the apparatus for its application, but from here on explanations will be provided concerning the concrete molding, manufactured by the present invention's method and the apparatus for the manufacture of moldings with core.

The moldability in the present invention could be defined by hardness and friability, etc. Here, in case that hardness is below 3 kg or friability is above 1% per 100 revolutions, the moldability are defined as low and a molding with low moldability is defined as a defective molding.

Furthermore, "friability" as term in the field of techniques for manufacturing of medical supplies, denotes the ability of the molded tablet to endure vibration and shock during transportation as well as the ability to endure the next process of coating, which ability is measured by the decreased amount of tablet weight, using a friability testing mechanism with a revolving drum. More specifically, following reference information "Method for testing friability of tablet" of Japanese Pharmacopoeia 13, second revised appendix (same as USP 24 General/information <1216> TABLET FRIABILITY), a drum with an electrical mechanism is set to revolve with 24 to 26 revolutions per minute, the weight of the tablet before and after a fixed cumulative number of revolutions is measured and calculated percentage of the decreased weight of tablet as compared with the weight of tablet in the beginning is called degree of friability. In the present invention friability is measured by changing the cumulative number of revolutions.

Next, degree of hardness is one index to appraise hardness of the tablet. Testing methods to measure degree of hardness of tablet include an unbreakability testing method, where kinetic elasticity rate is measured by super sonic waves, and breakability testing methods such as testing breakability under compression, strain testing, shock testing, etc. In medicine and food products fields, the method for testing breakability under pressure is employed most often. "Hardness" in the present description denotes hardness tested by the method for testing breakability under pressure. The method for testing breakability under pressure is to measure the load to break a tablet by pressurizing on both sides of the tablet in diameter direction. In other words, it is a method to show moldability of the tablet from combined force at the breaking section of the tablet.

Next, in the present description, the term "main ingredient" includes active molding material (effective molding material, main ingredient) in medical products field and main ingredient in food products field; all other molding material except main ingredient that is usually used as additives in medicine manufacturing techniques are united under the term "excipient, etc." and include excipient, binder, disintegrator, lubricant, agglutination preventing agent, etc.

A characteristic of the molding with core of the present invention is that they consist of a core part and an outer layer part, molded in one body. Here molding in one body means compression molding performed by a series of steps, using one set of punches and die only. The traditional a molding with core were manufactured by molding of a core in advance and in a different molding machine and then supplying it halfway through the molding step of moldings with core. For this reason moldings in one body carries contrasting implication.

In the molding with core of the present invention, molding material with poor moldability and molding material with good moldability can be distributed unevenly, which is to say it is possible to have a molding with core that maintain moldability only in the outer layer, while in the core the molding is incomplete. Here an incomplete molding, as defined above, a molding with degree of hardness below 3 kg or a molding with degree of friability over 1% per 100 revolutions. In the molding with core of the present invention it is possible to lower the moldability of core part even further, so as to produce a molding with core with degree of hardness of core below 2 kg or level of friability over 1% per 25 revolutions. It is possible to lower the moldability of the core part even further, so as to produce a molding with core with degree of hardness of core below 1 kg or degree of friability over 5% per 25 revolutions. The moldability of the outer layer are the very thing that determines the moldability of the whole molding, so as its degree of hardness is above 3 kg and degree of friability is below 1% per 100 revolutions, there are no problems with the moldability of the whole molding.

For example, as in medical products and foods fields, usually the main ingredient is of poor moldability, in the present invention a molding with core it is possible to put the greater part of main ingredient with poor moldability in the core and to feed excipient with good moldability as a greater part of the outer layer. In other words it is possible to make a molding with core that contain over 80% main ingredient and below 20% excipient in the core and below 20% main ingredient and over 80% excipient in the outer layer.

It is also possible to make a molding with core, where, after whole among of main ingredient is molded into core, the amount of excipient in the core is made below 20% or below 10% and the outer layer is made only of excipient of good moldability. Furthermore, it is also possible to make a molding with core, where the core is made only of main ingredient with poor moldability, or of main ingredient and lubricant (including excipient that can produce effect like that of lubricant), or of main ingredient and agglutination preventing agent (including excipient that can produce effect like that of agglutination preventing agent), or of main ingredient, lubricant and agglutination preventing agent in other words a molding with core where the core is made only of main ingredient and no excipient that improve moldability are included. Thus, breakability and solubility of active molding material can also be improved.

Since the a molding with core in the present invention are manufactured by molding in one body, there is no offset in positioning of the core as in the traditional molding with core, it is possible to make the outer layer extremely thin and there is no unevenness between the different moldings. Therefore it is possible to make the thickness of the outer layer in all parts below 1 mm or even below 0.9 mm, and also to manufacture such moldings with core on a large scale. In other words, the usefulness of the moldings with core of the present invention becomes even clearer when they are taken as multiple aggregate, so they could be represented as an aggregate of moldings with core, where thickness of the outer layer in all parts is below 1 mm or even below 0.9 mm. Thinning of the outer layer contributes to the miniaturization of a molding. Here the outer layer is the part, decided by the opening between the central punch and the die (the thickness of the outer punch tip part) and is defined as an outer layer part on the side of a molding, formed on the plane vertical to diameter plane of the molding (plane, perpendicular to the direction of pressurization) (FIG. 13, 80). Even in the prior art the thickness of the vertical section of a molding outer layer could be controlled by the amount of powder granule supplied, so by the superiority of the present invention is displayed reducing the thickness of the molding to the thickness of outer layer.

In the present description an aggregate denotes multiple moldings, manufactured on a large scale. Speaking in details, it is possible that the aggregate includes, for example, more that 100 moldings, or, in some cases more than 1000 or more than 10000.

Next follows a detailed explanation of the application of the present invention's molding with core in medical products and foods field.

The shape of the present invention's molding with core is not restricted, as far as it is easy to hold and to swallow, but in medical products field medicines with circular or oval shape are preferable.

The size of the present invention's molding with core is not unified, since there is difference between the individual moldings, as far as they are easy to swallow and, for example, in case of circular tablet it should be below 13 mm in diameter, in general between 4 mm to 13 mm in diameter and preferably between 5 mm to 11 mm in diameter. However, when a molding that is to be chewed is manufactured, the shape and the size should be measured so as to enable insertion into the oral cavity and easy chewing for example in case of circular tablet, the size should be below 25 mm in diameter, generally between 4 mm to 25 mm in diameter and preferably between 6 mm to 16 mm in diameter.

As far as the size of the core part is concerned, in order to prevent increase in the size of the whole molding, it is preferable to make the core as small as possible, but in order to perform the step of molding of core smoothly, it is not preferable to make it too small. Finally, in case of circular tablet, the core should be between 2 mm to 11 mm in diameter, preferably between 3 mm to 9 mm in diameter. However, when a molding that is to be chewed is manufactured, the size of the core in case of circular tablet for example should be below 23 mm in diameter, generally between 2 mm to 23 mm in diameter, preferably between 4 mm to 14 mm in diameter.

The shape of the core depends on the shape of the central punch, but in general it is in keeping with the above shape of the molding with core.

The thickness of the compression covering layer, in correspondence with the size of the core should be with low friability and ability to maintain the shape of molding and usually it is between 1 mm to 2.5 mm, but in this method for molding in one body, it could be below 1 mm, or even below 0.9 mm. However, when a molding that is to be chewed is manufactured, since it is better not to raise the degree of hardness more than necessary, it is preferable to make the compression covering layer as thin as possible, but enough thick so that to have low friability and to be able to maintain the shape of the molding.

Molding material that can maintain the shape of molding with core and that can be taken orally should be selected as molding material for the compression covering layer. There are no special restrictions, but is better to use one or combination of two molding materials with good compression moldability. The following excipients and binders can be described as molding material with good compression moldability: crystalline cellulose, lactose, sorbitol, maltitol, powderd hydrogenated maltose starch syrup, calcium hydrogen phosphate, anhydrous calcium hydrogen phosphate, silicate aluminate magnesium, meta silicate aluminate magnesium (all the above are excipient, following are binder), hydroxipropylcellulose, hydroxipropylmethylcellulose, alpha starch, carboxyvinyl polymers, polyvinyl alcohols, polyvinyl pyrrolidone, methylcellulose, gum arabic, pullulan, etc. Among them, preferable are crystalline cellulose and sorbitol.

In the compression covering layer and the core of molding with core in the present invention, different types of additives, generally used in medicine manufacturing techniques, can be used, such as excipient, binding agent, disintegrator, lubricant, agglutination preventing agent, etc. (combined under the common term "excipient, etc."). These additives can be used in amount, which is within the limits of their usual use in the field of medicine manufacturing techniques. However molding material that cannot be used in medicines and foods differ.

The excipients and binding agents are recorded as molding material with good compression moldability. As disintegrators carboxymethylcellulose calcium, cross-carmellose calcium, low substitution degree hydroxypropylcellulose, polyvinyl pyrrolidone, etc. can be described; as lubricants and agglutination preventing binders magnesium stearate, sucrose fatty acid ester, hydrate dioxide silicon etc., can be described.

The medical active molding material that appropriate the main part of the molding with core in the present invention are not subjected to special limitations, as long as they could be administered orally, but the following could be recorded as medicines with strong effect: medicines that affect the central nervous system, medicines that affect the circulatory organs, medicines that affect the respiratory organs, medicines that affect the digestive organs, antibiotics as well as chemical treatment medications, medicines that affect the metabolism, vitamins, antacids, etc. One type, two types and more of these medicines can be used. Most of their active molding material are of poor moldability so they cannot be molded separately.

The functional food molding material that appropriate the main part of the molding with core in the present invention are not subjected to special limitations, as long as they could be administered orally. The following molding material can be described as functional food molding material: molding material that affect the control of physical condition rhythm, molding material that affect the bio-defense, molding material that affect the disease prevention, molding material that affect the recovery from diseases and molding material that affect the suppression of ageing. One type, two types and more of these active food molding material can be used.

The general food molding material that appropriate the main part of the molding with core in the present invention are not subjected to special limitations, as long as they could be administered orally. Sweets and seasonings can be described as related foods.

These medical active molding material, functional food molding material and general food molding material (all defined with the common term "main ingredient"), are contained mainly in the core of the molding with core of the present invention, and if necessary, part of them could be put also in the compression covering layer, which is the outer layer. The combination amount of these main ingredient in the core should be determined according to the effective dosage of active molding material in the used medications or functional foods. The same goes for the general food molding material and there are no special limitations, but the combination amount should be between 30 to 100% of the mass of the core and the preferable amount is 60 to 100% of the mass of the core.

Furthermore, the molding material in the core and the compression covering layer could be used as they are, but, by following the general method, once the molding material could also be granulated and powder granule could be adjusted and then used. The powder granule together with the binding agents could also coat on an inactive carrier the medical active molding material, functional food molding material and general food molding material.

Next follows a simple explanation of the application of the products of the present invention in the fields of electronic parts, agricultural chemistry, sanitary products, etc.

In these cases, unlike in case of the medical products and foods, where the size and shape of the molding with core and the size and shape of the core should be made so as to enable insertion of the products in the oral cavity, the size and shape of molding with core and the size and shape of core are not subjected to any special limitations and as far as the shape of the punches allows, they should be made so as to suit the functions and the purpose of the molding with core. The same goes for the thickness of the compression covering layer, which should be made so as to maintain the moldability. The molding material of the core is also not subjected to any special limitations and anything that suits the functions and the purpose of the molding with core is allowed.

Next follows a detailed explanation of the molding with core in the present invention, accompanied by practical examples.

Experimental Example 1

Manufacture Example 1

On the surface of the punches of a double structure with inside diameter of 8.5 mm and outside diameter of 10.0 mm and with pressurizable flat edge, a small amount of magnesium stearate (manufactured by Taihei Kagaku Sangyo) was applied and as the lower central punch was kept in lowered position, in the space above the lower central punch, enclosed by the lower outer punch, 15 mg crystalline cellulose (manufactured by Asahi Kasei: Avicel PH-101) was supplied; then the upper central punch and the lower central punch were moved towards each other and compression was applied manually so as the surface to become flat. Next, as the lower central punch was kept in lowered position, in the space above the temporary moldings of crystalline cellulose, enclosed by the lower outer layer, 300 mg of ascorbic acid (manufactured by Merck Japan: L-ascorbic acid crystal) were supplied; then the upper central punch and the lower central punch were moved towards each other and temporary compression was applied manually so as to be able to maintain the molding shape. Next, as the bottom layer was kept in lowered position, in the space in the die above and around the molding, made of crystalline cellulose and ascorbic acid, the remaining 60 mg of crystalline cellulose (manufactured by Asahi Kasei: abicell PH-101) were supplied and the temporary ascorbic acid moldings were completely enclosed in crystalline cellulose; then the upper central punch and the lower central punch were moved towards each other and, using a hydraulic hand press (manufactured by Shimazu Seisakusho: SSP-10A), the tablet was made with compression force of about 1.4 ton. Weight of the tablets was 375 mg per tablet, thickness of the tablet was 3.40 mm and thickness of the outer layer was 0.75 mm.

Comparative Manufacture Example 1

375 mg of ascorbic acid (the same as above) were weighed and filled in the die and then, using a punch with 10.0 mm in diameter flat edge with magnesium stearate (the same as above), applied on the surface of both the upper and the lower punches and a rotary tableting machine (manufactured by Hata Tekkojo: HT-AP18SSII), by applying pressure of about 1.4 ton on the punches, tablet was made manually. Weight of the tablets was 372 mg per tablet, and thickness of the tablet was 3.40 mm.

Comparative Manufacture Example 2

150 g of ascorbic acid (the same as above) and 37.5 g of crystalline cellulose were mixed in 100 revolutions by a micro V shaped mixer (manufactured by Tsutsui Rikagaku Kiki). 375 mg of the mixture were weighed and filled in the die and then, using a punch with 10.0 mm flat edge with magnesium stearate (the same as above), applied on the surface of both the upper and the lower punches and a rotary tableting machine (the same as above), by applying pressure of about 1.4 ton on the punches, tablet was made manually. Weight of the tablets was 374 mg per tablet and thickness of the tablet was 3.41 mm.

Evaluation of Friability 1
Evaluation of friability of the tablets of the manufacture example and the comparative manufacture examples was performed in accordance with reference information "Method for testing friability of tablet" of Japanese Pharmacopoeia 13, second revised appendix (same as USP 24 General/information <1216> TABLET FRIABILITY) and using a drum with electrical mechanism (ELECTROLAB: EF1-W). Hardness of tablets was measured using a device for measuring breakability strength (manufactured by Toyama Kagaku). The results are shown in Table 1.

TABLE 1

| Samples | Number of cumulative revolutions of drum | | | | | Hardness of tablets (kg) |
| --- | --- | --- | --- | --- | --- | --- |
| | 25 | 100 | 250 | 375 | 500 | |
| Manufacture example 1 | 0.00 | 0.03 | 0.05 | 0.05 | 0.08 | 3.8 |
| Comparative manufacture example 1 | 9.28 | — | — | — | — | 0.7 |
| Comparative manufacture example 2 | 0.05 | 0.91 | 4.09 | 5.89 | 7.91 | 3.9 |

* Numbers in the columns show degree of friability. The unit is percents.
* "—" stands for impossibility to measure.

From the table 1 it becomes obvious that when the cumulative number of revolutions of the drum exceeds 25, the tablets with ascorbic acid of comparative manufacture example 1 break and the degree of friability cannot be measured, which shows that ascorbic acid is ingredient with extremely poor moldability. It could be surmised that the core part of manufacture example 1 also is with very poor moldability. The same tendency was noticed in respect to the degree of hardness of the tablets.

Although manufacture example 1 and comparative manufacture example 2 contained the same amount of ascorbic acid with extremely poor moldability and the excipient molding materials were also the same amount and same type, the results for friability were very different. While in manufacture example 1 friability was unnoticed even after the drum made 500 revolutions, in comparative manufacture example 2 about 8% of the tablet's weight was worn out. From the above results it became clear that when molding materials with low friability and poor moldability are molded, if the molding are the same as in manufacture example 1, friability could be improved immensely.

Experimental Example 2

The results of experimental example 1 showed that the tablets of manufacture example 1 possess superb degree of friability.

The combination proportion of ascorbic acid and crystalline cellulose, which would allow the same degree of friability as in manufacture example 1 while weight of the tablet is unchanged, in the traditional methods for manufacturing of ordinary tablets (same as comparative manufacture example 2) was evaluated.

Comparative Manufacture Example 3

131.5 g of ascorbic acid (manufactured by Merck Japan: L-ascorbic acid crystals) and 56 g of crystalline cellulose (manufactured by Asahi Kasei: abisel PH-1) were mixed at 100 revolutions in a micro V-shaped mixer (manufactured by Tsutsui Rikagaku Kiki). 375 mg of the mixture were weighed and filled in the die and then, using a punch with 10.0 mm in diameter flat edge with magnesium stearate (manufactured by Taihei Kagaku Sangyo), applied on the surface of both the upper and the lower punches and a rotary tableting machine (manufactured by Hata Tekkojo: HT-AP18SSII), by applying pressure of about 1.4 ton on the punches, a tablet was made manually. Weight of the tablets was 374 mg per tablet.

Comparative Manufacture Example 4

112.5 g of ascorbic acid (the same as above) and 75 mg of crystalline cellulose (the same as before) were mixed in a micro V-shaped mixer (the same as before) at 100 revolutions. 375 g of the mixture were weighed and filled in a die and then, using a punch with 10.0 mm flat edge with magnesium stearate (the same as above), applied on the surface of both upper and lower punches and a rotary tableting machine (the same as before), by applying pressure of about 1.4 ton on the punches, a tablet was made manually. Weight of the tablet was 375 mg.

Comparative Manufacture Example 5

93.7 g of ascorbic acid (the same as before) and 93.8 g of crystalline cellulose (the same as before) were mixed in a micro V-shaped mixer (the same as before) at 100 revolutions. 375 g of the mixture were weighed and filled in a die and then, using a punch with 10.0 mm flat edge with magnesium stearate (the same as above), applied on the surface of both upper and lower punches and a rotary tableting machine (the same as before), by applying pressure of about 1.4 ton on the punches, a tablet was made manually. Weight of the tablet was 375 mg.

Evaluation of Friability 2

The evaluation of friability was performed according to the previous evaluation of friability 1. The results are shown in table 2.

TABLE 2

| Samples | Number of cumulative revolutions of drum | | | | | Hardness of tablets (kg) |
|---|---|---|---|---|---|---|
| | 25 | 100 | 250 | 375 | 500 | |
| Comparative manufacture example 2 80:20 | 0.05 | 0.91 | 4.09 | 5.89 | 7.91 | 3.9 |
| Comparative manufacture example 3 70:30 | 0.08 | 0.24 | 0.62 | 1.56 | 2.74 | 6.9 |
| Comparative manufacture example 4 60:40 | 0.00 | 0.05 | 0.16 | 0.21 | 0.32 | 11.5 |
| Comparative manufacture example 5 50:50 | 0.00 | 0.05 | 0.03 | 0.05 | 0.05 | 16.5 |
| Manufacture example 1 80:20 | 0.00 | 0.03 | 0.05 | 0.05 | 0.08 | 3.8 |

* Numbers in the columns show degree of friability. The unit is percents.
* The ration below the type of testing shows proportion of the combination ascorbic acid: crystalline cellulose.

Table 2 shows that in order to achieve same friability as in manufacture example 1 at the same weight of tablets, using traditional methods for manufacturing (comparative manufacture examples 2 to 5) the proportion ratio of ascorbic acid that is of poor moldability and of crystalline cellulose that improves moldability should be 50:50. In other words, as compared with tablets, manufactured according to the traditional methods, where the amount of ascorbic acid must be decreased in order to solve the problems with friability, in the tablets, manufactured by the present invention, that have same degree of friability at the same weight (manufacture example 1), the amount of ascorbic acid could be 1.6 times the amount of ascorbic acid in the tablets, manufactured according to the traditional methods. From these results it becomes clear that when the amount of ascorbic acid in the compression-coated tablets of the present invention is kept the same, the tablets could be made smaller and lighter.

From the comparison between the weight of tablets of manufacture example 1 and of tablets of comparative manufacture example 5, that have almost the same degree of friability, it becomes clear that the tablets of the present invention (manufacture example 1) have superb degree of friability, but despite this their hardness does not increase more than necessary, so they are very suitable for chewing.

Experimental Example 3

The results of manufacture example show that the tablets of comparative manufacture example 1 have poor moldability and high degree of friability. For this reason evaluation of the pros and cons of manufacturing of compression-coated tablets with poor moldability by the traditional manufacturing methods was performed (comparative manufacture example 6). The core supplying mechanism of the compression-coated tablets making mechanism (manufactured by Hata Tekkojo: HT-AP33-C) cannot be applied for formatting the tablets in the comparative manufacture example 1 (there are problems with supplying the core pills in the die), so the shape of the tablets was changed to 6.5 mm in diameter ordinary R and ascorbic acid was used, which is same as comparative manufacture example 6.

Comparative Manufacture Example 6

748 g of ascorbic acid (manufactured by Merck Japan: L-ascorbic acid crystals) and 2 g magnesium stearate (manufactured by Taihei Kagaku Sangyo) were mixed at 100 revolutions in small V-shaped mixer (manufactured by Tsutsui Rikagaku Kiki). The mixture is compressed in a rotary tableting machine (manufactured by Hata Tekkojo: HT-AP18SSII), using punch of 6.5 mm in diameter ordinary R and by applying pressure of about 0.7 ton on the punch and then is made into tablets. The weight of the tablets made was 101 mg per tablet and the degree of hardness was 0.3 kg. Some of the tablets broke during the handling and it was impossible to measure the degree of friability. Breaking and wearing out of tablets in the supply route, in the die or on the table were feared and therefore the decision was that compression-coated tablets, manufactured following the traditional methods, are impossible.

Results

When compression-coated tablets are of poor moldability, there are problems such as breaking and wearing out of the tablets in the supply route, so manufacturing of compression-coated tablets by the traditional methods was impossible.

Experimental Example 4

Experimental example 3 showed that when only ascorbic acid is used as ingredient for core, due to insufficient moldability of the core it is impossible to make tablets using the traditional device for making tablets (manufactured by Hata Tekkojo: HT-AP33-C). The same test was performed, using taurine as ingredient for compression-coated tablets.

Manufacture Example 2

On the surface of punches of a double structure with inside diameter of 8.5 mm and outside diameter of 10.0 mm and with flat edge, small amount of magnesium stearate (manufactured by Taihei Kagaku Sangyo) was applied and as the lower central punch was kept in lowered position, in the space above the lower central punch, enclosed by the lower outer punch, 30 mg crystalline cellulose (manufactured by Asahi Kasei: abicell PH-101) was supplied; then the upper central punch and lower central punch were moved towards each other and temporary compression was applied manually so as the surface to become flat. Then, as the lower central punch was kept in lowered position, in the space above the temporary moldings of crystalline cellulose, enclosed by the lower outer layer, 300 mg taurine (manufactured by Iwaki Seiyakujo: taurine "Iwaki" aminoethyl sulfonic acid) were supplied; then the upper central punch and the lower central punch were moved towards each other and temporary compression was applied manually so as to maintain moldings. Next, as the lower punch was in lowered position, in the space above and around the temporary moldings of crystalline cellulose and taurine, the remaining 70 mg crystalline cellulose (the same as above) were fed so that the temporary moldings of taurine was completely enclosed in crystalline cellulose; then the upper punch and the lower punch were moved towards each other and tablets were made by compression of about 1.4 ton, using hydraulic type hand press device (manufactured by Shimazu Seisakusho: SSP-10A). The weight of tablets was 393 mg per tablet, the thickness of the tablets was 3.92 mm and the thickness of the outer layer was 0.75 mm.

Comparative Manufacture Example 7

300 mg of taurine (the same as above) were weighed and filled in the die and then, using a punch with 8.5 mm flat edge with small amount of magnesium stearate (the same as above), applied on the surface of both upper and lower punches and a rotary tableting machine (manufactured by Hata Tekkojo: HT-AP18SSII), tablets were made manually with compression of about 1.5 ton per punch. The weight of the tablets was 299 mg per tablet and their thickness was 3.78 mm.

Evaluation of Friability 3

Table 3 shows that the taurine containing tablets of comparative manufacture example 7 are completely destroyed before the cumulative number of revolutions of the drum reaches 25 and the degree of friability cannot be measured, which means that taurine is an ingredient with extremely poor moldability. The same tendency was confirmed for the hardness of the tablets. From this results it became clear that in the traditional way of making compression-coated tablets the moldability of core were not good and therefore it is impossible to supply core, made only of taurine.

In contrast to that, the compression-coated tablets of the present invention of the manufacture example 2 have superb degrees of friability, despite the fact that the core is made only of taurine with very poor moldability and in the same amount as in the comparative manufacture example 7.

TABLE 3

| Samples | Number of cumulative revolutions of drum | | | | | Hardness of tablets (kg) |
|---|---|---|---|---|---|---|
| | 25 | 100 | 250 | 375 | 500 | |
| Manufacture example 2 | 0.00 | 0.25 | 0.51 | 0.76 | 0.76 | 4.1 |
| Comparative manufacture example 7 | — | — | — | — | — | 0.7 |

* The values in the columns show degree of friability in percents.
* "—" shows impossibility to measure.

Next follow explanations of the molding with core having plural cores, as part of the molding with core of the present invention. The molding with core having plural cores of the present invention is molding with plural cores having an outer layer and plural cores inside the layer which are integrally molded. One of the features is that the plural of cores is placed vertically towards the compression plane of the molding. Here compression plane is the plane assumed to be vertical to the direction of pressurization by punches, which accepts the compression. The direction, vertical to the compression plane of the molding is the same as the direction of compression of molding.

Plural cores means more than two cores, usually two to several cores, and the cores could be multiplied by simple repetition of the steps of molding of the core (outer layer and cores repeated molding step). Cores exist in the molding not only in connected form, but it is also possible to separate them by outer layer, or even to make plural cores of the same molding material as well as plural cores of different molding material. Thus in the field of medicines, for example, it is possible to separate two or more types of molding material that are feared to have side effects into different core.

Another characteristic of the molding having plural cores is that the positioning of the cores is unified and they are distributed in specific positions. The traditional methods also allowed manufacturing of molding having plural cores, but the positioning of the cores was different for each molding so it was impossible to manufacture on a large scale molding having plural cores, where the cores were distributed to specific unified positions. Therefore the usefulness of the molding having plural cores becomes even clearer when they are made into aggregates and the expression aggregates of moldings having plural cores, characterized by unified and specific positioning of the cores could be used.

Thus, in the molding having plural cores in the present invention, the plural cores is distributed in decided positions, the outer layer could be made as thin as possible and therefore further miniaturization of the molding is possible.

The previous explanations of the molding with core of the present invention can be applied without changes for the molding having plural cores of the present invention.

Next follow more detailed explanations of molding with core that contain microcapsules and coated particles, as part of the molding with core of the present invention. In the present description microcapsules and capsulated particles, which have lost their specifics, characteristics and functions due to their poor moldability, high brittleness or damage, are called with the generic name particle clusters and are defined as microcapsule type granule. In other words, the microcapsule type granule include every kind of coated granule such as microcapsules, seamless capsules, and mini-soft capsules, micro-spheres, as well as macromolecular coated granule, wax coated granule, sugar coated granule, etc. There is also microcapsule type granule, which includes granule that is feared to lose their activity in high-compression process of making tablets and that can be formed as one-functional units, such as acetic ingredients containing granule, etc. The coated granule of every kind is granule with coating on the granule particle, granule in the granule particle of which there is a core, granule in the granule particle of which there is a core and which have coating on the granule particle, and granule whose purpose is to improve their controlled release properties, lipid solubility, easy solubility, heat resistance, light resistance as well as stability and bitter taste.

The microcapsule type of granule that are used in this field are usually with diameter below 3 mm, preferably below 2 mm, and even below 1 mm. However, if they are granule that can be formed as functional units, the diameter is not subject to any special restrictions.

The structure of the molding with core of the present invention is characterized by core part, which contains microcapsule type of granule, and outer layer, which covers the core and is a compression-covering layer. Here the microcapsule type granule is in state of a multiplicity of aggregates. Preferably the outer layer should not include microcapsule type granule, but mainly molding material with superb moldability, which is to say that preferably the whole amount of microcapsule type granule should be contained in the core. It is possible that the outer layer contains small amount of microcapsule type granule, but is not preferable from content uniformity point of view.

The present invention succeeds in manufacturing of the molding, containing microcapsule type granule, where microcapsule type of granule, which is of poor moldability, is distributed unevenly in the core part and the outer layer is composed of molding material of superb moldability, where microcapsule type of granule is contained in large amounts in the molding, due to inserting molding material of superb moldability between the microcapsule type granule in the core and thus it succeeds in improving substantially the moldability and the friability of the molding. The present invention also achieves easily the degree of friability of molding, prescribed by reference information "Method for testing friability of tablet" of Japanese Pharmacopoeia 13, second revised appendix (same as USP 24 General/information <1216> TABLET FRIABILITY), which is below 1%. At the same time by decreasing as much as possible the fed amount of excipients it enabled the miniaturization of the molding. Furthermore, since the core in the present invention's molding with core, containing microcapsule type granule, is distributed in a specific position, there are no offsets and the outer layer could be made extremely thin, which also contributes to the miniaturization of the molding.

Speaking in details, in the present invention's molding with core, containing microcapsule type granule, the moldability depend mainly on the molding material of the outer layer and therefore molding material with superb moldability are fed mainly in the outer layer. Furthermore, by inserting molding material with superb moldability in the microcapsule type granule in the core, or in other words, by feeding separately molding material of superb moldability in the core, the moldability of the core are secured. In order to secure the moldability of the core, while preventing the increase in size of the molding, the preferable fed amount of molding material with superb molding amounts in the core should be between 10 and 120% by mass of the microcapsule type of granule in the core. As a result, it is possible even with low compression to manufacture molding with superb moldability and degree of friability, and there is no necessity to perform granulation of the microcapsule type granule in order to secure the moldability. Thus, it is possible to avoid problems such as damages of the capsule of the microcapsule type granule or of the granule itself, due to outer pressure during steps of granulation and making of tablet.

The molding material with superb moldability, used in the present invention, are not subjected to any special limitations, but it is preferable if they are molding material that can achieve sufficient moldability at low pressure during making the tablets and these molding materials can be used separately or in combinations. Such molding materials of superb moldability are the same as described above.

Furthermore, in the molding with core, containing microcapsule type granule, of the present invention, the traditional method of feeding mixed excipients and microcapsule type granule in the die are not used, but instead it is possible to apply the method of feeding separately in the die the microcapsule type granule and the molding material of superb moldability, such as excipients. Thus it is possible to avoid problems such as segregation of microcapsule type granule and excipients. Therefore, the molding with core, containing microcapsule type granule, of the present invention is molding with core with superb even distribution of the microcapsule type granule in the molding and can be said to be aggregates of moldings with core, containing microcapsule type granule, characterized by unified amount of microcapsule type granule in the core. Here unified amount denotes amount which is in conformity of Experimental method for unified amount of Japanese Pharmacopoeia General Testing Methods $13^{th}$ Revision.

The size and shape of the molding with core, containing microcapsule type granule, of the present invention are not subjected to any special restrictions, as far as they are in the allowed limits for manufacturing by the punch, and they can be made following the previous explanations of molding with core and in accordance with their application. The same goes for the size and shape of the core, but in order to secure its moldability it is not preferable to make the core too big against the size of the whole molding, which is to say to make the outer layer too thin. To maintain the moldability, the thickness of the outer layer should be above 1 mm.

Next follow detailed explanations accompanied by execution examples, using microcapsules as microcapsule type granule. The measuring methods of the physical properties of the tablet, the amount of microcapsules and the difference in color of tablet are also shown below.

Method for Measuring Degree of Friability (%)

Manufacture example and comparative manufacture example evaluation of tablets friability was performed using drum with electrical mechanism (ELECTROLAB: EF1-W), following the "Method for testing friability of tablet" of Japanese Pharmacopoeia 13, second revised appendix (same as USP 24 General/information <1216> TABLET FRIABILITY). The drum revolutions were set to 24 to 26 revolutions per minute, then the weight of tablets was measured before and after a fixed cumulative number of revolutions and the percentage of diminished weight against the weight of the tablets in the beginning was calculated as degree of friability.

Method for Measuring Content of Microcapsules (%)

The content of microcapsules was calculated by measuring the weight of the microcapsules. First, the tablets or the mixture were precisely measured, then the tablets or the mixture were sieved using ethanol with a 48 Mesh sieve and the microcapsules only were separated. Then the separated microcapsules were dried and precisely measured, the weight of the microcapsules was divided by the previously measured whole tablets or mixture and the calculated percentage was the amount of microcapsules.

Color Difference of Tablets (ΔE)

The color difference of front and back of tablets was measured using color difference meter (manufactured by MINOLTA: CM3500d) The method to measure color difference was to calculate the difference between samples, defined by ΔL, Δa, Δb, which represent the difference of coordinates L*, a*, b* in the color surface system L*a*b*. The result was the color difference (ΔE*a b). Hereinafter (ΔE*a b) will be abbreviated to (ΔE).

Evaluation of Destruction of Microcapsules during Tablet Molding Step

The examination, judging whether the microcapsules were destructed or not was performed by visual observation of whether the surface of the tablets is colored or not, after tablets, containing microcapsules with vitamin E and then immediately after the molding the vitamin E (tocopherol) is oozed out.

Experimental Example 5

Using degree of friability as index, the moldability of the tablet was evaluated in reference to the following manufacture examples: the present invention's manufacture example 1M, with compression-coated tablet where microcapsules are sandwiched by excipients in the form of a layer; comparative manufacture example 1M, where tablet is made by mixing physically microcapsules and excipients; comparative manufacture example 2, where microcapsules are sandwiched by excipients in the form of a layer; comparative manufacture example 3, where tablet is made as molding with core, without sandwiching the microcapsules by excipients in the form of a layer.

Manufacture Example 1M

On the surface of the punches of a double structure with inside diameter of 6.0 mm and outside diameter of 8.0 mm and with flat edge, small amount of magnesium stearate (manufactured by Taihei Kagaku Sangyo) was applied and, as the lower central punch was kept in lowered position, in the space above the lower central punch, enclosed by the lower outer punch 30 mg of granulated product of lactose and crystalline cellulose (manufactured by MEGGLE: Cellactose 80) were supplied; then the upper central punch and the lower central punch were moved towards each other and compression was applied manually so as the surface to become flat. Then, as the lower central punch was kept in lowered position, in the space above the temporary moldings of lactose and crystalline cellulose, enclosed by the lower outer punch, 30 mg microcapsules (manufactured by Rikyuu Vitamins: beads of vitamin E and C) were fed; then the upper central punch and the lower central punch were moved towards each other and temporary compression was applied manually so as the surface to become flat. Next, in the space above the temporary moldings made of the previously molded lactose and crystalline cellulose and microcapsules, enclosed by lower outer punch, 50 mg of granulated product of lactose and crystalline cellulose were fed; then the upper central punch and the lower central punch were moved towards each other and temporary compression was applied manually so as the surface to become flat. Next, in the space above the temporary moldings, made in the previous steps, the remaining 30 mg of microcapsules were supplied; then the upper central punch and the lower central punch were moved towards each other and in the next step of temporary molding was performed to a degree, which could maintain moldability, enabling smooth transition. Finally, as the lower punch was kept in lowered position, in the space above and around the temporary moldings, made in the previous steps, the remaining 60 mg of granulated product of lactose and crystalline cellulose (manufactured by MEGGLE: Cellactose 80) were fed and as the temporary moldings made of lactose and crystalline cellulose and microcapsules were completely enclosed in the granulated product of lactose and crystalline cellulose, the lower punch and the upper punch were moved towards each other and using hydraulic type hand press (manufactured by Iuchi Seieido: 3 ton high pressure jack), tablets were made, applying on a tablet unit of square measure pressure of 7.9 kg/mm² (approximately 400 kg per punch). The weight of the tablets was 197.1 mg per tablet and the thickness of the tablets was 3.54 mm. There was no oozing out of vitamin E on the surface of the pills, so it was confirmed that there was no destruction of microcapsules.

Comparative Manufacture Example 1M 60 mg of microcapsules (the same as above) and 140 mg of granulated product of lactose and crystalline cellulose (the same as above) were weighed and after being mixed manually in a small bag with a fastener, the whole amount is filled in a die. Using a punch of 8.0 mm in diameter with flat edge, on the surface of the upper and lower punches of which small amount of magnesium stearate (the same as before) was applied and a hydraulic type hand press (the same as before), tablets were made, applying on a tablet unit of square measure pressure of 7.9 kg/mm² (approximately 400 kg per punch). The weight of the tablets was 194.6 mg per tablet and the thickness of the tablets was 3.52 mm. There was no oozing out of vitamin E on the surface of the pills, so it was confirmed that there was no destruction of microcapsules.

Comparative Manufacture Example 2M

On the surface of both the upper and lower punches of a double structure with outside diameter of 8.0 mm and with flat edge, small amount of magnesium stearate (the same as before) was applied and, as the lower punch was kept in lowered position, 50 mg of granulated product of lactose and crystalline cellulose (the same as before) was supplied; then the upper punch and the lower punch were moved towards each other and temporary compression was applied manually so as the surface to become flat. Next, as the lower punch was kept in lowered position, in the space over the temporary moldings of lactose and crystalline cellulose in the die, 30 mg of microcapsules (the same as above) were supplied; then the upper punch and the lower punch were moved towards each other and temporary compression was applied manually so as the surface to become flat. Next, in the space over the temporary moldings, made of lactose and crystalline cellulose and microcapsules in the die, 40 mg of granulated product of lactose and crystalline cellulose were fed; then the upper punch and the lower punch were moved towards each other and temporary compression was applied manually so as the surface to become flat. Furthermore, in the space above the molding, made in the previous steps, the remaining 30 mg of microcapsules were fed and the upper punch and the lower punch were moved towards each other and compression was applied manually so as the surface to become flat. Finally, in the space in the die above the temporary moldings, the remaining 50 mg of lactose and crystalline cellulose were supplied and using hydraulic type hand press (the same as before), tablets were made, applying on a tablet unit of square measure pressure of 7.9 kg/mm² (approximately 400 kg per punch). The weight of the tablets was 195.4 mg per tablet and the thickness of the tablets was 3.51 mm. When taken out of the die, on the surface (circumference plane) of this tablet there was a big crack in the microcapsule layer and upon taking hold of them with hand during or after taking them out, the layer collapsed.

Comparative Manufacture Example 3M

On the surface of both the upper and lower punches of a double structure with inside diameter of 6.0 mm and outside diameter of 8.0 mm and with flat edge, small amount of magnesium stearate (the same as before) was applied and, as the lower central punch was kept in lowered position, in the space above the lower central punch and enclosed by the lower outer punch 55 mg of granulated product of lactose and crystalline cellulose (the same as above) were supplied; then the upper central punch and the lower central punch were moved towards each other and temporary compression was applied manually so as the surface to become flat. Next, as the lower central punch was kept in lowered position, in the space above the temporary moldings of lactose and crystalline cellulose, enclosed by the lower outer layer, 60 mg of microcapsules (the same as above) were supplied; then the upper central punch and the lower central punch were moved towards each other and in the next step of temporary molding was performed to a degree, which could maintain moldability, enabling smooth transition. Next, as the lower punch was kept in lowered position, in the die, in the space above and around the temporary moldings formed in the previous steps, the remaining 85 mg of granulated product of lactose and crystalline cellulose (the same as above) were supplied and as the temporary moldings of lactose and crystalline cellulose and microcapsules was completely enclosed in the granulated product of lactose and crystalline cellulose, upper punch and lower punch were moved towards each other and, using hydraulic type hand press (the same as before), tablets were made, applying on a tablet unit of square measure pressure of 7.9 kg/mm² (approximately 400 kg per punch). The weight of the tablets was 198.8 mg per tablet and the thickness of tablets was 3.56 mm. When taken out of the die, on the surface (circumference plane) of this tablet there was a big crack in the microcapsule layer and upon taking hold of them with hand during or after taking them out, the layer collapsed. Besides, on a part of the tablet's surface there was a small amount of microcapsules.

Evaluation of Friability

The results of the friability test are shown in Table 4. Despite the fact that manufacture example 1M, comparative manufacture example 1M, comparative manufacture example 2M and comparative manufacture example 3M contain the same amount of molding materials of extremely poor moldability and the used excipients are also of same content and amount, and, furthermore, the force of the pressure applied is the same, the degree of friability differed substantially. As compared with manufacture example 1, where even after 100 revolutions of the drum, there was almost no friability, in comparative manufacture example 1M approximately 10% of the weight of the tablet were worn out. Furthermore, in comparative manufacture example 2M and 3M, immediately after manufacturing the tablets, there were damages in the layer and the friability couldn't be evaluated so manufacturing of moldings was impossible.

TABLE 4

| Samples | Number of cumulative revolutions of drum | | | |
|---|---|---|---|---|
| | 25 | 50 | 75 | 100 |
| Manufacture example 1M | 0.00% | 0.10% | 0.25% | 0.51% |
| Comparative manufacture example 1M | 0.77% | 2.62% | 4.27% | 10.02% |
| Comparative manufacture example 2M | — | — | — | — |
| Comparative manufacture example 3M | — | — | — | — |

* The numbers (%) in the columns show degree of friability
* "—" shows impossibility to measure The main reason for the increase in friability in comparative manufacture example 1M is the exfoliation of the microcapsules on the surface of the tablets and the reason for the collapse in the layer in comparative manufacture example 2M is that microcapsules without moldability were distributed up to the outer part of the moldings and that part became fragile and as a result the moldability of the whole moldings decreased. Next, the reason for the collapse in the layers in comparative manufacture example 3M is that the large amount of microcapsules without moldability couldn't be supported by the outer layer alone. These results show that when moldings large amount of microcapsules with poor moldability, if the moldings with core are like the ones in manufacture example 1M, then friability can be improved substantially.

Experimental Example 6

The results of experimental example 5 showed that the tablets of manufacture example 1M possess superb degree of friability. Next, tablets, containing large amount of microcapsules were manufactured by the conventional method of manufacturing ordinary tablets and the uniformity of the microcapsules' amount in the tablets as well as their outer look were evaluated.

Comparative Manufacture Example 4M 150 g microcapsules (the same as above) and 345 g granulated product of lactose and crystalline cellulose (the same as above) are mixed in small-type V-shaped mixer (manufactured by Tsutsui Rikagaku Kiki) at 100 revolutions. Then 5 g of magnesium stearate are fed in the mixture and it is mixed again at 50 revolutions. Next, samples are taken from one place in the bottom layer, 2 places in the middle layer and 3 places in the upper layer of the mixture in the small-type V-shaped mixer and are used as samples for measuring the amount of microcapsules.

The mixture samples are made into tablets, using a punch with 6.0 mm in diameter ordinary R and in rotary device for making pills (manufactured by Kikusui Seisakujo: VIRGO518SSII AZ), applying pressure of 10.6 kg/mm² per tablet unit square measure (approximately 300 kg per punch). These tablets were used as samples in comparative manufacture example 4M. These samples were gathered at the beginning of the process of making the tablets (0 minute), 10 min, 20 min, 30 min and at the end of the process of making the tablets (40 min) and thus approximately 100 samples of tablets were made. The average weight of the tablets was approximately 78 mg and the thickness of the tablets was approximately 3.8 mm. In all samples there was no oozing out of vitamin E on the surface of the tablets and lack of breaking of microcapsules was confirmed.

Evaluation of Uniformity of Content

The results of the evaluation of content's uniformity, performed in accordance with the method for measuring microcapsule content, are shown on table 5. It became clear that when tablets, containing large amount of microcapsules are made in sequence by the traditional methods, the amount of microcapsules in the tablets changes substantially. In other words, it became clear that the microcapsule content of the tablets in comparative manufacture example 4M decreased in the beginning of the step of making tablets and increased in the end of the same step. It was surmised that this change in the amount followed the following pattern: the microcapsules in the excipients were separated in the upper part due to the oscillation and the rotation of the device for making tablets and that is why in the beginning of the process of making tablets the excipients were in large amount, but with the passage of time the excipients in the lower part disappeared and the microcapsules, which existed in the upper part were filled in the die and that is why the amount increased. Furthermore, the change in the microcapsules amount was also related to the change in the pressure during the process of making tablets and it became clear that it is extremely difficult to perform stable step of making tablets in sequence.

TABLE 5

| Samples of comparative manufacture example 4M | Average amount of microcapsules (%) in 1 tablet | Ratio (%) against the average amount of mixture |
| --- | --- | --- |
| Mixture | 29.7 ± 5.1 | 100 |
| At the beginning of tabletting step 0 min | 34.8 ± 2.0 | 116.9 ± 7.2 |
| 10 min | 19.1 ± 1.9 | 64.2 ± 6.2 |
| 20 min | 19.0 ± 1.5 | 64.0 ± 5.2 |
| 30 min | 43.8 ± 2.1 | 147.2 ± 7.0 |
| At the end of tabletting step 40 min | 43.0 ± 0.9 | 144.7 ± 2.9 |

* The theoretical value of microcapsule content in one tablet is 30%.
* The number of samples of mixture is n = 6, the number of samples of tablets is n = 3 and ± shows standard deviation The unevenness in the microcapsule content already became obvious in the mixture for measuring microcapsule content and changed according to the difference of the places of the samples between 24.6 and 34.8% against the theoretical amount of molding material (30%). It was confirmed that even if the time of mixing was changed, the unevenness couldn't be improved (this data is not shown).

On the other hand, in the present invention, in manufacturing molding like the ones shown in manufacture example 1M, the traditional methods of mixing excipients and microcapsules and then feeding them in the die are not used, but instead new methods of feeding the microcapsules and excipients separately in the die are applied and that is why problems such as segregation of microcapsules and excipients do not occur. In other words, the uniformity of content is in compliance with the method for testing uniformity of content in 13$^{th}$ revision of Japanese Pharmacopoeia, General Testing Methods.

From the results given above it became clear that in the tablets, manufactured following the traditional method for physical mixing, there was substantial unevenness in the content of microcapsules and uniformity of content couldn't be secured.

Evaluation of Existence/Nonexistence of Both Sides of Tablets

The results of the measurement of the color difference of both sides of the tablets, performed following the above methods, are shown in Table 6.

TABLE 6

| Samples of comparative manufacture example 4M | Average value of color difference (ΔE) of one tablet |
| --- | --- |
| At the beginning of tabletting step 0 min | 0.9 ± 0.6 |
| 10 min | 0.6 ± 0.3 |
| 20 min | 1.1 ± 0.6 |
| 30 min | 6.9 ± 1.5 |
| At the end of the step of making tablets 40 min | 5.8 ± 2.2 |

* The number of sample tablets is n = 3, ± shows standard deviation.

This results show that when tablets, containing large amount of microcapsules, are made in sequence, following the traditional method, on both sides of the tablet or in other words on the surface of the tablet appears a large amount of microcapsules. In general, when the color difference value exceeds "3", the difference in the color should be clearly visible, but it became clear that the distinction in both sides (color difference over 3) appears at the end of the step of making tablet and is related with the previously described change in the content. That distinction in both sides creates problems not only with the outer look of the tablet, but also shows that microcapsules without moldability are concentrated at the surface of the tablet and therefore arises new problems of abrasion of the microcapsules.

On the other hand, in the molding of the present invention, like the ones shown in manufacture example 1M, due to the method if the invention, microcapsules do not appear in the outer layer and therefore problems, typical for the prior art, such as abrasion of microcapsules from the tablets or appearance of microcapsules on the both sides, are successfully avoided.

Up to here the present invention's method for the manufacture of a molding with core, the apparatus necessary for it's application and the molding with core, which are it's product were explained in details, but the technical scope of the present invention is not limited to the above execution form.

The effectiveness of the present invention could be summarized as follows: since it enables moldings at once of moldings with core from molding material as contrasted to the supplying of core, manufactured beforehand as moldings, the present invention has not only high production efficiency, but also enables to avoid different troubles related to the core and makes possible the manufacturing of molding with extremely low levels of unevenness and high precision which guarantees high quality of the product.

Furthermore, in the present invention it is possible to manufacture moldings with core, where the core is made of molding material that couldn't be molded by the traditional method and also to apply the alternative method of film coating, used in the field of medical products for masking the bitter taste, improving the outer look and elution control.

What is claimed is:

1. A method for manufacturing a molding with a core using compression molding apparatus that comprises an upper punch and a lower punch which are arranged in the vertical direction of a die, wherein each of the upper punch and the lower punch has a double structure comprising a central punch and an outer punch surrounding the outer periphery of the central punch, wherein both the central punch and the outer punch are capable of independent sliding motions as well as compressing operations, the method comprising:

positioning the lower central punch with respect to the lower outer punch to create a space above the lower central punch and inside the lower outer punch;

supplying a first unmolded molding material into the space above the lower central punch and inside the lower outer punch, and onto an upper surface of the lower outer punch from a feeding shoe;

driving the lower central punch and the upper central punch to compression mold the first molding material; between the lower central punch and the upper central punch, wherein the upper outer punch is spaced a certain distance from the lower outer punch, and wherein said spacing substantially prevents contact between the upper outer punch and the lower outer punch and between the upper outer punch and the first molding material;

discharging pressured air and/or applying suction to remove unmolded first molding material residue on the lower outer punch while the molded first molding material is gripped and held in place between the lower central punch and the projected upper central punch;

positioning the lower central punch with respect to the lower outer punch to create a space above the molded first molding material and inside the lower outer punch;

supplying a second unmolded molding material into the space above the molded first molding material and inside the lower outer punch, and onto an upper surface of the lower outer punch from a feeding shoe;

driving the lower central punch and the upper central punch to compression mold the first and second molding materials between the lower central punch and the upper central punch, wherein the upper outer punch is spaced a certain distance from the lower outer punch, and wherein said spacing substantially prevents contact between the upper outer punch and the lower outer punch and between the upper outer punch and the second molding material;

discharging pressured air and/or applying suction to remove unmolded second molding material residue on the lower outer punch while the molded first and second molding materials are gripped and held in place between the lower central punch and the projected upper central punch;

positioning the lower central punch and the lower outer punch to create a space above the molded first and second molding materials and the lower outer punch in the die;

supplying a third unmolded molding material into the space above the molded first and second molding materials and the lower outer punch in the die from a feeding shoe to completely envelope the molded second molding material with the first and third molding materials;

driving the upper punch and the lower punch together to compression mold the whole of the first, second, and third molding materials in the die; and taking out the compressed molding comprising the first, second, and third molding materials as a unit from the compression molding apparatus.

2. The method of claim 1, wherein the first and third molding materials have substantially the same composition.

3. The method of claim 1, wherein each of the molding materials is in the form of powder or granules.

* * * * *